US010390738B2

(12) United States Patent
Clark et al.

(10) Patent No.: US 10,390,738 B2
(45) Date of Patent: Aug. 27, 2019

(54) SYSTEMS AND METHODS FOR DYNAMICALLY IDENTIFYING A PATIENT SUPPORT SURFACE AND PATIENT MONITORING

(71) Applicant: CareView Communications, Inc., Lewisville, TX (US)

(72) Inventors: Matt Clark, Frisco, TX (US); Derek del Carpio, Corinth, TX (US); Kenneth Chapman, Charlotte, NC (US)

(73) Assignee: CareView Communications, Inc., Lewisville, TX (US)

( * ) Notice: Subject to any disclaimer, the term of this patent is extended or adjusted under 35 U.S.C. 154(b) by 0 days.

(21) Appl. No.: 16/031,004

(22) Filed: Jul. 10, 2018

(65) Prior Publication Data

US 2019/0008416 A1    Jan. 10, 2019

Related U.S. Application Data

(63) Continuation of application No. 15/409,002, filed on Jan. 18, 2017, now Pat. No. 10,045,716, which is a
(Continued)

(51) Int. Cl.
*H04N 7/18* (2006.01)
*H04N 13/02* (2006.01)
(Continued)

(52) U.S. Cl.
CPC ............ *A61B 5/1115* (2013.01); *A61B 5/002* (2013.01); *A61B 5/0077* (2013.01); *A61B 5/1117* (2013.01); *A61B 5/1128* (2013.01); *A61B 5/7275* (2013.01); *A61B 5/746* (2013.01); *A61B 5/7475* (2013.01); *G06F 19/00* (2013.01); *G06T 7/136* (2017.01); *G06T 7/70* (2017.01); *G06T 7/97* (2017.01); *A61B 2576/00* (2013.01);
(Continued)

(58) Field of Classification Search
CPC .... A61B 5/002; A61B 5/1115; H04N 13/0203
USPC ............ 348/143, 46, 42, 77, 47, 208.14, 61; 382/103; 705/2, 3
See application file for complete search history.

(56) References Cited

U.S. PATENT DOCUMENTS

| 9,579,047 | B2* | 2/2017 | Clark | A61B 5/002 |
| 10,045,716 | B2* | 8/2018 | Clark | A61B 5/002 |
| 2013/0184592 | A1* | 7/2013 | Venetianer | H04N 7/18 |
| | | | | 600/476 |

* cited by examiner

*Primary Examiner* — Jefferey F Harold
*Assistant Examiner* — Jean W Desir
(74) *Attorney, Agent, or Firm* — Seth H. Ostrow; Meister Seelig & Fein LLP

(57) ABSTRACT

Various patient monitoring systems can include a sensor configured to collect three dimensional information. The systems can identify a location of a patient support surface based on the three dimensional information. The systems can set a two dimensional planar threshold based on the patient support surface. The systems can identify a patient location above the patient support surface based on the three dimensional information and compare the patient location to the two dimensional planar threshold. Exceeding the threshold can be indicative of a high risk of a patient fall. An alert can be generated based on the threshold being exceeded. The systems can repeat the identification of the patient support surface location and the setting of the threshold to account for changes in the patient area.

20 Claims, 11 Drawing Sheets

Related U.S. Application Data continuation of application No. 14/209,726, filed on Mar. 13, 2014, now Pat. No. 9,579,047.

(60) Provisional application No. 61/792,204, filed on Mar. 15, 2013.

(51) Int. Cl.
*A61B 5/11* (2006.01)
*A61B 5/00* (2006.01)
*G06T 7/136* (2017.01)
*G06T 7/00* (2017.01)
*G06T 7/70* (2017.01)
*G06F 19/00* (2018.01)

(52) U.S. Cl.
CPC ............... *G06T 2207/10016* (2013.01); *G06T 2207/10028* (2013.01)

SYSTEMS AND METHODS FOR DYNAMICALLY IDENTIFYING A PATIENT SUPPORT SURFACE AND PATIENT MONITORING

CROSS REFERENCE TO RELATED APPLICATIONS

The present application is a continuation of U.S. patent application Ser. No. 15/409,002, entitled "SYSTEMS AND METHODS FOR DYNAMICALLY IDENTIFYING A PATIENT SUPPORT SURFACE AND PATIENT MONITORING," filed on Jan. 18, 2017, which is a continuation of co-pending U.S. patent application Ser. No. 14/209,726, filed Mar. 13, 2014, which claims the benefit of priority of U.S. Provisional Patent Application No. 61/792,204, filed Mar. 15, 2013, the entirety of which are hereby incorporated by reference.

FIELD OF INVENTION

The present disclosure relates to systems and methods for patient monitoring by analyzing three dimensional information to detect patient events.

BACKGROUND

Healthcare facilities rely on patient monitoring to supplement interventions and reduce the instances of patient falls. Constant eyes-on monitoring of patients can be difficult for healthcare professionals to maintain. Video monitoring can be used to automate patient monitoring and increase the ability of a healthcare professional to effectively monitor a group of patients distributed between different rooms. Various systems and methods for patient video monitoring have been disclosed, such as U.S. Patent Application No. 2009/0278934 entitled System and Method for Predicting Patient Falls, U.S. Patent Application No. 2010/0134609 entitled System and Method for Documenting Patient Procedures; U.S. Patent Application No. 2012/0026308 entitled System and Method for Using a Video Monitoring System to Prevent and Manage Decubitus Ulcers in Patients, and U.S. Provisional Patent Application No. 61/707,227 entitled System and Method for Monitoring a Fall State of a Patient and Minimizing False Alarms.

Various routines can be run by a monitoring system to automatically detect patient events. For example, a system can monitor a patient in a bed and issue an alert if the patient falls or otherwise leaves the bed. Monitoring systems have generally used cameras that monitor patients in two dimensions, typically reducing a scene to a flat image. Various features and algorithms have been developed to accurately monitor patient events occurring in three dimensions with cameras that reduce the scenes to two dimensions. For example, a two dimensional camera can be set up to view a scene that includes a hospital bed. A user can identify one or more zones within the scene associated with risk to the patient. For example, the zones can be aligned with the edges of the bed where a patient is at risk of falling from the bed. An algorithm can then process image information within the zones over time to detect changes within the zones indicative of patient movement. Such systems can be effective in patient monitoring but also can have several limitations. For example, the two dimensional images may lack depth information such that shadows can be interpreted as patient movement. Also, because the zones may be aligned with a bed or other area, changes to the scene (e.g., movement of the bed) may require that the zones be realigned. Boundaries between similarly colored areas at different depths can be difficult to detect using two dimensional techniques. There is a need for monitoring systems that can interpret scenes in three dimensions and automatically adapt to changes in the scenes.

SUMMARY

In example 1, a patient monitoring system for monitoring a patient area, the system comprising: a sensor configured to output a plurality of frames, the plurality of frames containing three dimensional information of the patient area; a user interface; and control circuitry configured to: receive the three dimensional information of the plurality of frames; identify a location of a patient support surface based on the three dimensional information; set at least one height threshold to correspond to at least one area directly above the location of the patient support surface; identify one or more patient locations directly above the patient support surface based on the three dimensional information; compare the one or more patient locations to the at least one height threshold; and generate an output with the user interface based on the one or more patient locations being above the at least one height threshold.

In example 2, the patient monitoring system of example 1, wherein the control circuitry is configured to repeat the identifying the location of the patient support surface and the setting of the at least one height threshold steps to dynamically adjust the location of the at least one height threshold to account for changes in the location of the patient support surface.

In example 3, the patient monitoring system of example 2, wherein the control circuitry is configured to repeat the identifying the location of the patient support surface and the setting of the at least one height threshold periodically based on one or both of expiration of a timer and reception of a predetermined number of the plurality of frames.

In example 4, the patient monitoring system of either of examples 1 or 2, wherein each of the at least one area is a predetermined distance directly above the patient support surface.

In example 5, the patient monitoring system of any preceding example, wherein the control circuitry is configured to identify a plurality of planes of the patient support surface, wherein the plurality of planes are contiguous and non-coplanar.

In example 6, the patient monitoring system of example 5, wherein the at least one height threshold comprises a plurality of height thresholds, and the control circuitry is configured to set each of the plurality of height thresholds to correspond to a respective one of a plurality of different areas, the plurality of different areas respectively located directly above the plurality of planes.

In example 7, the patient monitoring system of example 6, wherein the control circuitry is configured to select the output for generation from a plurality of different outputs, the selection based on which of the plurality of height thresholds the one or more patient locations is above.

In example 8, the patient monitoring system of example 6, wherein the plurality of different outputs correspond to different patient risk levels.

In example 9, the patient monitoring system of any preceding example, wherein the three dimensional information comprises a plurality of pixels.

In example 10, the patient monitoring system of example 9, wherein the control circuitry is configured to separate the plurality of pixels into a first set and a second set based on the pixels of the first set being directly above the patient support surface and the pixels of the second set not being directly above the patient support surface.

In example 11, the patient monitoring system of example 10, wherein the control circuitry is configured to identify the one or more patient locations based on the first set while ignoring the second set.

In example 12, the patient monitoring system of example 9, wherein the control circuitry is configured to identify the one or more patient locations by grouping at least some of the pixels of the plurality of pixels.

In example 13, the patient monitoring system of any preceding example, wherein the control circuitry is configured to identify the patient support surface based on a patient support surface buffer comprising the three dimensional information aggregated from a predetermined number of frames, wherein the identification of the patient support surface is updated based on the reception of each frame of the plurality of frames.

In example 14, the patient monitoring system of any preceding example, wherein the control circuitry is configured to identify the one or more patient locations based on a patient location buffer comprising the three dimensional information aggregated from a predetermined number of frames, wherein the identification of the one or more patient locations is updated based on the reception of each frame of the plurality of frames.

In example 15, the patient monitoring system of any preceding example, wherein the output comprises an alert indicative of a heightened risk of the patient falling.

In example 16, the patient monitoring system of any preceding example, wherein identifying the patient support surface comprises identifying an object from the three dimensional information that corresponds with one or more template characteristics.

In example 17, a method for processing a chronological series of frames containing three dimensional information generated by a camera to monitor a patient in a patient area by performing the following steps, each step performed at least in part by a computing system: receiving the three dimensional information of the plurality of frames; identifying a location of a patient support surface based on the three dimensional information; setting at least one height threshold to correspond to at least one area directly above the location of the patient support surface; identifying one or more patient locations directly above the patient support surface based on the three dimensional information; comparing the one or more patient locations to the at least one height threshold; and generating an output with the user interface based on the one or more patient locations being above the at least one height threshold.

In example 18, the method of example 17, further comprising repeating the identifying the location of the patient support surface and the setting of the at least one height threshold steps to dynamically adjust the location of the at least one height threshold to account for changes in the location of the patient support surface.

In example 19, the method of either of examples 17 or 18, further comprising repeating the identifying the location of the patient support surface and the setting of the at least one height threshold periodically based on one or both of expiration of a timer and reception of a predetermined number of the plurality of frames.

In example 20, the method of any of examples 17-19, wherein each of the at least one height thresholds is a predetermined distance directly above the patient support surface.

In example 21, the method of any of examples 17-20, further comprising identifying a plurality of planes of the patient support surface, wherein the plurality of planes are contiguous and non-coplanar.

In example 22, the method of example 21, wherein the at least one height threshold comprises a plurality of height thresholds, and each height threshold of the plurality of height thresholds is set to correspond to a respective one of a plurality of different areas, the plurality of different areas respectively located directly above the plurality of planes.

In example 23, the method of example 22, further comprising selecting the output for generation from a plurality of different outputs, the selection based on which of the plurality of height thresholds the one or more patient locations is above.

In example 24, the method of example 23, wherein the plurality of different outputs correspond to different patient risk levels.

In example 25, the method of any of examples 17-24, wherein the three dimensional information comprises a plurality of pixels.

In example 26, the method of example 25, further comprising separating the plurality of pixels into a first set and a second set based on the pixels of the first set being directly above the patient support surface and the pixels of the second set not being directly above the patient support surface.

In example 27, the method of example 26, wherein the identification of the one or more patient locations is based on the first set.

In example 28, the method of example 25, further comprising grouping at least some of the pixels of the plurality of pixels, wherein the identification of the one or more patient locations is based on the grouping.

In example 29, the method of any of examples 17-28, further comprising aggregating the three dimensional information from a predetermined number of frames in a buffer, wherein identifying the location of the patient support surface comprises determining a nominal location of the patient support surface based on the aggregation of the three dimensional information.

In example 30, the method of any of examples 17-29, further comprising aggregating the three dimensional information from a predetermined number of frames in a buffer, wherein the one or more patient locations are updated based on the reception of each frame of the plurality of frames.

In example 31, the method of any of examples 17-30, wherein the output comprises an alert indicative of a heightened risk of the patient falling.

In example 32, the method of any of examples 17-31, wherein identifying the patient support surface comprises identifying an object from the three dimensional information that corresponds with one or more template characteristics.

In example 33, a patient monitoring system for monitoring a patient area, the system comprising: a sensor configured to output a plurality of frames, the plurality of frames containing three dimensional information of the patient area; a user interface; and control circuitry configured to: receive the three dimensional information of the plurality of frames; identify a location of a patient support surface based on the three dimensional information; set at least one lower threshold to correspond to at least one two dimensional plane below and laterally offset from the location of the patient support surface; identify one or more patient locations based on the three dimensional information; compare the one or more patient locations to the at least one lower threshold; and generate an output with the user interface based on the one or more patient locations traversing the at least one lower threshold.

In example 34, the patient monitoring system of example 33, wherein the control circuitry is configured to repeat the identifying the location of the patient support surface and the setting of the at least one lower threshold steps to dynamically adjust the location of the at least one lower threshold to account for changes in the location of the patient support surface.

In example 35, the patient monitoring system of example 34, wherein the control circuitry is configured to repeat the identifying the location of the patient support surface and the setting of the at least one lower threshold periodically based on one or both of expiration of a timer and reception of a predetermined number of the plurality of frames.

In example 36, the patient monitoring system of any of examples 33-35, wherein each of the at least one area is a predetermined distance below the patient support surface.

In example 37, the patient monitoring system of any of examples 33-36, wherein the at least one lower threshold comprises a plurality of lower thresholds, and the control circuitry is configured to set the plurality of lower thresholds on opposite sides of the patient support surface.

In example 38, the patient monitoring system of any of examples 33-37, wherein the three dimensional information comprises a plurality of pixels.

In example 39, the patient monitoring system of example 38, wherein the control circuitry is configured to separate the plurality of pixels into a first set and a second set based on the pixels of the first set being directly above any of the patient support surface or the at least one lower threshold, and the pixels of the second set not being directly above any of the patient support surface or the at least one lower threshold.

In example 40, the patient monitoring system of example 39, wherein the control circuitry is configured to identify the one or more patient locations based on the first set while ignoring the second set.

In example 41, the patient monitoring system of example 38, wherein the control circuitry is configured to identify the one or more patient locations by grouping at least some of the pixels of the plurality of pixels.

In example 42, the patient monitoring system of any of examples 33-41, wherein the control circuitry is configured to identify the patient support surface based on a patient support surface buffer comprising the three dimensional information aggregated from a predetermined number of frames, wherein the identification of the patient support surface is updated based on the reception of each frame of the plurality of frames.

In example 43, the patient monitoring system of any of examples 33-42, wherein the control circuitry is configured to identify the one or more patient locations based on a patient location buffer comprising the three dimensional information aggregated from a predetermined number of frames, wherein the identification of the one or more patient locations is updated based on the reception of each frame of the plurality of frames.

In example 44, the patient monitoring system of any of examples 33-43, wherein the output comprises an alert indicative of a heightened risk of the patient falling.

In example 45, the patient monitoring system of any of examples 33-44, wherein identifying the patient support surface comprises identifying an object from the three dimensional information that corresponds with one or more template characteristics.

In example 46, a method for processing a chronological series of frames containing three dimensional information generated by a camera to monitor a patient in a patient area by performing the following steps, each step performed at least in part by a computing system: receiving the three dimensional information of the plurality of frames; identifying a location of a patient support surface based on the three dimensional information; setting at least one lower threshold to correspond to at least one two dimensional plane below and laterally offset from the location of the patient support surface; identifying one or more patient locations based on the three dimensional information; comparing the one or more patient locations to the at least one lower threshold; and generating an output with the user interface based on the one or more patient locations traversing the at least one lower threshold.

In example 47, the method of example 46, further comprising repeating the identifying the location of the patient support surface and the setting of the at least one lower threshold steps to dynamically adjust the location of the at least one lower threshold to account for changes in the location of the patient support surface.

In example 48, the method of either of examples 46 or 47, further comprising repeating the identifying the location of the patient support surface and the setting of the at least one lower threshold periodically based on one or both of expiration of a timer and reception of a predetermined number of the plurality of frames.

In example 49, the method of any of examples 46-48, wherein each of the at least one lower threshold is a predetermined distance below the patient support surface.

In example 50, the method of any of examples 46-49, wherein the at least one lower threshold comprises a plurality of lower thresholds, and the plurality of lower thresholds are set on opposite sides of the patient support surface.

In example 51, the method of any of examples 46-50, wherein the three dimensional information comprises a plurality of pixels.

In example 52, the method of example 51, further comprising separating the plurality of pixels into a first set and a second set based on the pixels of the first set being directly above any of the patient support surface or the at least one lower threshold, and the pixels of the second set not being directly above any of the patient support surface or the at least one lower threshold.

In example 53, the method of example 52, wherein the identification of the one or more patient locations is based on the first set while the second set is ignored.

In example 54, the method of example 51, further comprising grouping at least some of the pixels of the plurality of pixels, wherein the identification of the one or more patient locations is based on the grouping.

In example 55, the method of any of examples 46-54, further comprising aggregating the three dimensional information from a predetermined number of frames in a buffer, wherein identifying the location of the patient support surface comprises determining a nominal location of the patient support surface based on the aggregation of the three dimensional information.

In example 56, the method of any of examples 46-55, further comprising aggregating the three dimensional information from a predetermined number of frames in a buffer, wherein the one or more patient locations are updated based on the reception of each frame of the plurality of frames.

In example 57, the method of any of examples 46-56, wherein the output comprises an alert indicative of a heightened risk of the patient falling.

In example 58, the method of any of examples 46-57, wherein identifying the patient support surface comprises identifying an object from the three dimensional information that corresponds with one or more template characteristics.

In example 59, a patient monitoring system for monitoring a patient area, the system comprising: a sensor configured to output a plurality of frames, the plurality of frames containing three dimensional information of the patient area; a user interface; and control circuitry configured to: receive the three dimensional information of the plurality of frames; identify a location of a patient support surface based on the three dimensional information, the patient support surface having a plurality of edges; set at least one vertical threshold, each vertical threshold corresponding to a respective vertical plane extending upward from a respective one of the plurality edges of the patient support surface; identify one or more patient locations directly above the patient support surface based on the three dimensional information; compare the one or more patient locations to the at least one vertical threshold; and generate an output with the user interface based on the one or more patient locations traversing the at least one vertical threshold.

In example 60, the patient monitoring system of example 59, wherein the control circuitry is configured to repeat the identifying the location of the patient support surface and the setting of the at least one vertical threshold steps to dynamically adjust the at least one vertical threshold to account for changes in the location of the patient support surface.

In example 61, the patient monitoring system of example 60, wherein the control circuitry is configured to repeat the identifying the location of the patient support surface and the setting of the at least one vertical threshold periodically based on one or both of expiration of a timer and reception of a predetermined number of the plurality of frames.

In example 62, the patient monitoring system of any of examples 59-61, wherein each respective vertical plane extends a predetermined distance above the patient support surface.

In example 63, the patient monitoring system of any of examples 59-62, wherein each respective vertical plane has a length equal to a length of the patient support surface.

In example 64, the patient monitoring system of any of examples 59-63, wherein the three dimensional information comprises a plurality of pixels.

In example 65, the patient monitoring system of example 64, wherein the control circuitry is configured to separate the plurality of pixels into a first set and a second set based on the pixels of the first set being directly above the patient support surface and the pixels of the second set not being directly above the patient support surface.

In example 66, the patient monitoring system of example 65, wherein the control circuitry is configured to identify the one or more patient locations based on the first set while ignoring the second set.

In example 67, the patient monitoring system of example 64, wherein the control circuitry is configured to identify the one or more patient locations by grouping at least some of the pixels of the plurality of pixels.

In example 68, the patient monitoring system of any of examples 59-67, wherein the control circuitry is configured to identify the patient support surface based on a patient support surface buffer comprising the three dimensional information aggregated from a predetermined number of frames, wherein the identification of the patient support surface is updated based on the reception of each frame of the plurality of frames.

In example 69, the patient monitoring system of any of examples 59-68, wherein the control circuitry is configured to identify the one or more patient locations based on a patient location buffer comprising the three dimensional information aggregated from a predetermined number of frames, wherein the identification of the one or more patient locations is updated based on the reception of each frame of the plurality of frames.

In example 70, the patient monitoring system of any of examples 59-69, wherein the output comprises an alert indicative of a heightened risk of the patient falling.

In example 71, the patient monitoring system of any of examples 59-70, wherein identifying the patient support surface comprises identifying an object from the three dimensional information that corresponds with one or more template characteristics.

In example 72, a method for processing a chronological series of frames containing three dimensional information generated by a camera to monitor a patient in a patient area by performing the following steps, each step performed at least in part by a computing system: receiving the three dimensional information of the plurality of frames; identifying a location of a patient support surface based on the three dimensional information, the patient support surface having a plurality of edges; set at least one vertical threshold, each vertical threshold corresponding to a respective vertical plane extending upward from a respective one of the plurality edges of the patient support surface; identifying one or more patient locations directly above the patient support surface based on the three dimensional information; comparing the one or more patient locations to the at least one vertical threshold; and generating an output with the user interface based on the one or more patient locations traversing the at least one vertical threshold.

In example 73, the method of example 72, further comprising repeating the identifying the location of the patient support surface and the setting of the at least one vertical threshold steps to dynamically adjust the location of the at least one vertical threshold to account for changes in the location of the patient support surface.

In example 74, the method of either of examples 72 or 73, further comprising repeating the identifying the location of the patient support surface and the setting of the at least one vertical threshold periodically based on one or both of expiration of a timer and reception of a predetermined number of the plurality of frames.

In example 75, the method of any of examples 72-74, wherein each respective vertical plane extends a predetermined distance above the patient support surface.

In example 76, the method of any of examples 72-75, wherein each respective vertical plane has a length equal to a length of the patient support surface.

In example 77, the method of any of examples 72-76, wherein the three dimensional information comprises a plurality of pixels.

In example 78, the method of example 77, further comprising separating the plurality of pixels into a first set and a second set based on the pixels of the first set being directly above the patient support surface and the pixels of the second set not being directly above the patient support surface.

In example 79, the method of example 78, wherein the identification of the one or more patient locations is based on the first set while the second set is ignored.

In example 80, the method of example 79, further comprising grouping at least some of the pixels of the plurality of pixels, wherein the identification of the one or more patient locations is based on the grouping.

In example 81, the method of any of examples 72-80, further comprising aggregating the three dimensional information from a predetermined number of frames in a buffer, wherein identifying the location of the patient support surface comprises determining a nominal location of the patient support surface based on the aggregation of the three dimensional information.

In example 82, the method of any of examples 72-81, further comprising aggregating the three dimensional information from a predetermined number of frames in a buffer, wherein the one or more patient locations are updated based on the reception of each frame of the plurality of frames.

In example 83, the method of any of examples 72-82, wherein the output comprises an alert indicative of a heightened risk of the patient falling.

In example 84, the method of any of examples 72-83, wherein identifying the patient support surface comprises identifying an object from the three dimensional information that corresponds with one or more template characteristics.

In example 85, a patient monitoring system for monitoring a patient area, the system comprising: a sensor configured to output a plurality of frames, the plurality of frames containing three dimensional information of the patient area; a user interface; and control circuitry configured to: receive the three dimensional information of the plurality of frames; identify a location of a patient support surface based on the three dimensional information; set at least one threshold, each of the at least one threshold comprising a two dimensional plane, each of the at least one threshold set at a respective location based on the location of the patient support surface; identify one or more patient locations based on the three dimensional information; compare the one or more patient locations to the at least one threshold; and generate an output with the user interface based on the one or more patient locations traversing the at least one threshold.

In example 86, the patient monitoring system of example 85, wherein the control circuitry is configured to repeat the identifying the location of the patient support surface and the setting of the at least one threshold steps to dynamically adjust the respective location of the at least one threshold to account for changes in the location of the patient support surface.

In example 87, the patient monitoring system of example 86, wherein the control circuitry is configured to repeat the identifying the location of the patient support surface and the setting of the at least one threshold periodically based on one or both of expiration of a timer and reception of a predetermined number of the plurality of frames.

In example 88, the patient monitoring system of any of examples 85-87, wherein the two dimensional plane of each at least one threshold has a length and a width.

In example 89, the patient monitoring system of example 88, wherein one or both of the length and the width are determined based on one or more dimensions of the patient support surface.

In example 90, the patient monitoring system of any of examples 85-89, wherein the at least one threshold comprises a height threshold that is set directly above the patient support surface such that the two dimensional plane of the height threshold extends parallel with the patient support surface.

In example 91, the patient monitoring system of any of examples 85-90, wherein the at least one threshold comprises a lower threshold that is set to correspond an area below and laterally offset from the location of the patient support surface.

In example 92, the patient monitoring system of any of examples 85-91, wherein the at least one threshold comprises a vertical threshold, the vertical threshold corresponding to a respective vertical plane extending upward from a respective one of a plurality edges of the patient support surface.

In example 93, the patient monitoring system of example 92, wherein the control circuitry is configured to select the output for generation from a plurality of different outputs, the selection based on which of the at least one threshold is traversed, the at least one threshold comprising the height threshold, the lower threshold, and the vertical threshold.

In example 94, the patient monitoring system of example 93, wherein the plurality of different outputs correspond to different patient risk levels.

In example 95, the patient monitoring system of any of examples 85-94, wherein the three dimensional information comprises a plurality of pixels.

In example 96, the patient monitoring system of example 95, wherein the control circuitry is configured to separate the plurality of pixels into a first set and a second set based on the pixels of the first set being above the patient support surface and the pixels of the second set not being above the patient support surface.

In example 97, the patient monitoring system of example 96, wherein the control circuitry is configured to identify the one or more patient locations based on the first set while ignoring the second set.

In example 98, the patient monitoring system of example 95, wherein the control circuitry is configured to identify the one or more patient locations by grouping at least some of the pixels of the plurality of pixels.

In example 99, the patient monitoring system of any of examples 85-98, wherein the control circuitry is configured to identify the patient support surface based on a patient support surface buffer comprising the three dimensional information aggregated from a predetermined number of frames, wherein the identification of the patient support surface is updated based on the reception of each frame of the plurality of frames.

In example 100, the patient monitoring system of any of examples 85-99, wherein the control circuitry is configured to identify the one or more patient locations based on a patient location buffer comprising the three dimensional information aggregated from a predetermined number of frames, wherein the identification of the one or more patient locations is updated based on the reception of each frame of the plurality of frames.

In example 101, the patient monitoring system of any of examples 85-100, wherein the output comprises an alert indicative of a heightened risk of the patient falling.

In example 102, the patient monitoring system of any of examples 85-101, wherein identifying the patient support surface comprises identifying an object from the three dimensional information that corresponds with one or more template characteristics.

In example 103, a method for processing a chronological series of frames containing three dimensional information generated by a camera to monitor a patient in a patient area by performing the following steps, each step performed at least in part by a computing system: receiving the three dimensional information of the plurality of frames; identifying a location of a patient support surface based on the three dimensional information; setting at least one threshold, each of the at least one threshold comprising a two dimensional plane, each of the at least one threshold set at a respective location based on the location of the patient support surface; identifying one or more patient locations based on the three dimensional information; comparing the one or more patient locations to the at least one threshold; and generating an output with the user interface based on the one or more patient locations traversing the at least one threshold.

In example 104, the method of example 103, further comprising repeating the identifying the location of the patient support surface and the setting of the at least one threshold steps to dynamically adjust the respective location of the at least one threshold to account for changes in the location of the patient support surface.

In example 105, the method of either of examples 103 or 104, further comprising repeating the identifying the location of the patient support surface and the setting of the at least one threshold periodically based on one or both of expiration of a timer and reception of a predetermined number of the plurality of frames.

In example 106, the method of any of examples 103-105, wherein the two dimensional plane of each at least one threshold has a length and a width.

In example 107, the method of example 106, wherein one or both of the length and the width are determined based on one or more dimensions of the patient support surface.

In example 108, the method of any of examples 103-107, wherein the at least one threshold comprises a height threshold that is set directly above the patient support surface such that the two dimensional plane of the height threshold extends parallel with the patient support surface.

In example 109, the method of any of examples 103-108, wherein the at least one threshold comprises a lower threshold that is set to correspond an area below and laterally offset from the location of the patient support surface.

In example 110, the method of any of examples 103-109, wherein the at least one threshold comprises a vertical threshold, the vertical threshold corresponding to a respective vertical plane extending upward from a respective one of a plurality edges of the patient support surface.

In example 111, the method of example 110, further comprising selecting the output for generation from a plurality of different outputs, the selection based on which of the at least one threshold is traversed, the at least one threshold comprising the height threshold, the lower threshold, and the vertical threshold.

In example 112, the method of example 111, wherein the plurality of different outputs correspond to different patient risk levels.

In example 113, the method of any of examples 103-112, wherein the three dimensional information comprises a plurality of pixels.

In example 114, the method of example 113, further comprising separating the plurality of pixels into a first set and a second set based on the pixels of the first set being directly above the patient support surface and the pixels of the second set not being directly above the patient support surface.

In example 115, the method of example 114, wherein the identification of the one or more patient locations is based on the first set.

In example 116, the method of example 113, further comprising grouping at least some of the pixels of the plurality of pixels, wherein the identification of the one or more patient locations is based on the grouping.

In example 117, the method of any of examples 103-116, further comprising aggregating the three dimensional information from a predetermined number of frames in a buffer, wherein identifying the location of the patient support surface comprises determining a nominal location of the patient support surface based on the aggregation of the three dimensional information.

In example 118, the method of any of examples 103-117, further comprising aggregating the three dimensional information from a predetermined number of frames in a buffer, wherein the one or more patient locations are updated based on the reception of each frame of the plurality of frames.

In example 119, the method of any of examples 103-118, wherein the output comprises an alert indicative of a heightened risk of the patient falling.

In example 120, the method of any of examples 103-119, wherein identifying the patient support surface comprises identifying an object from the three dimensional information that corresponds with one or more template characteristics.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
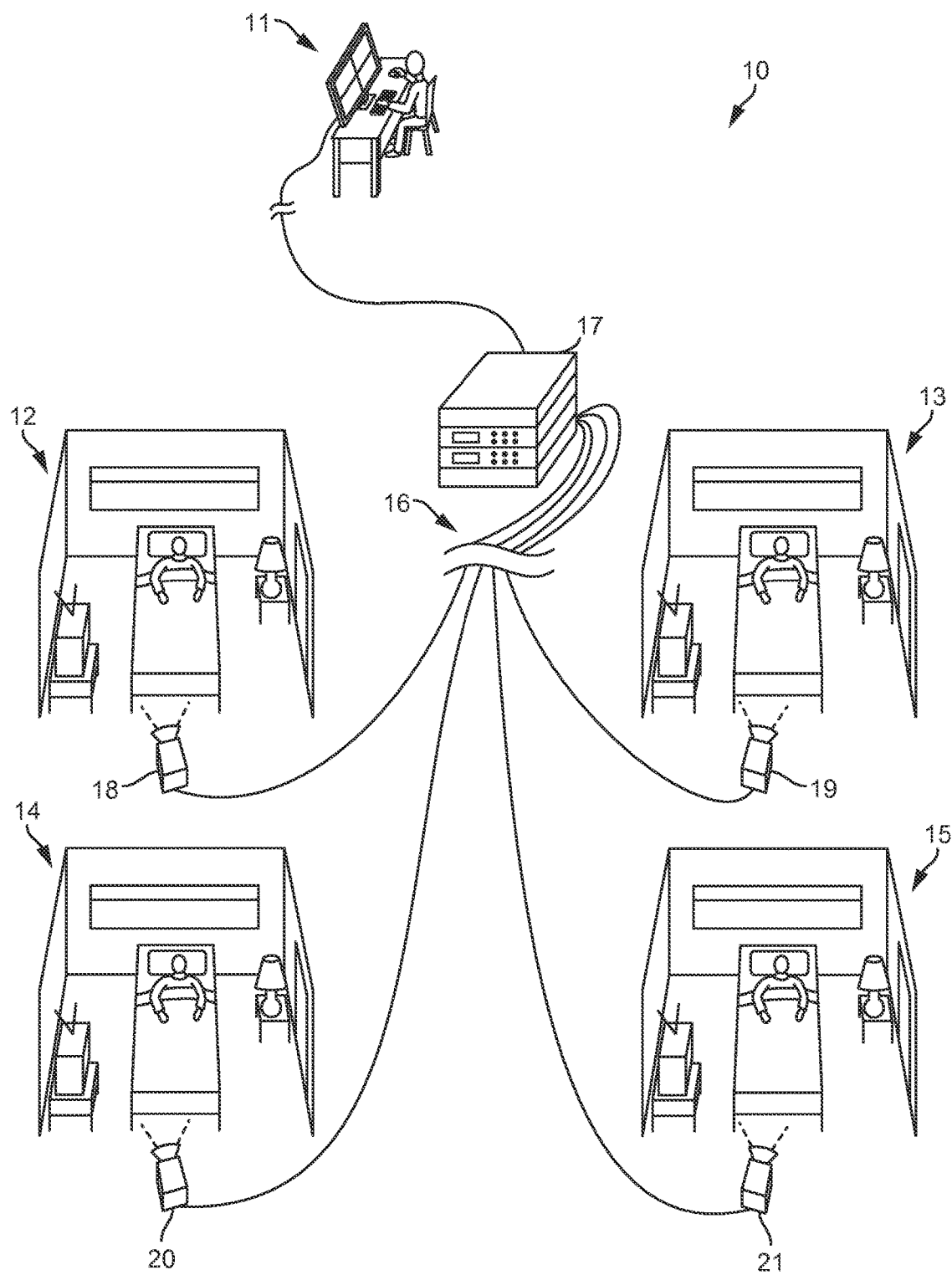
FIG. 1 is a schematic illustration of a monitoring system.

While the subject matter of the present disclosure is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Various embodiments of the present disclosure concern monitoring to detect patient events. Such events can concern situations in which a patient is at increased risk of injury or otherwise is in need of intervention. Patient events can include a patient at risk of falling, a patient falling (e.g., while leaving a bed), a patient at risk of ulcer formation or otherwise in need of repositioning, a patient in need of intervention, a patient outside of a designated area, and patient motion, among various other events.

FIG. 1 is a schematic diagram of a patient monitoring system 10. The patient monitoring system 10 can allow a healthcare professional to monitor multiple patient areas 12-15 from a monitoring station 11 via a computing system 17. The monitoring station 11 can comprise a user interface, which can include a screen and an input. The screen can display images of the patient areas 12-15, indications of one or more states of the patients being monitored, patient data, and/or other information. In some embodiments, the components of the monitoring station 11 are portable such that the monitoring station 11 can move with the healthcare professional.

While four patient areas 12-15 are shown in FIG. 1, any number of patient areas can be monitored at the monitoring station 11 via the computing system 17. The monitoring station 11 can be remote from the patient areas 12-15. For example, the monitoring station 11 can be on the same or different floor as the patient areas 12-15, in the same or different building as the patient areas 12-15, or located in a geographically different location as the patient areas 12-15. Furthermore, the patient areas 12-15 can be remote from each other. The computing system 17 can be in one particular location or the components of the computing system 17 can be distributed amongst multiple locations. The computing system 17 can be at the monitoring station 11 or can be remote from the monitoring station 11 and/or the patient areas 12-15.

As shown in FIG. 1, a plurality of cameras 18-21 can be respectively positioned to view and generate frames of the plurality of patient areas 12-15. Information concerning the frames, such as three dimensional pixel information, can be transmitted from the plurality of cameras 18-21 along data channels 16 to the computing system 17. In some cases, the computing system 17 is a single unit, such as a server or a personal computer (e.g., a desktop computer or a laptop computer). In some cases, the computing system 17 is distributed amongst several units, such as one or more personal computers, one or more servers, circuitry within one or more of the cameras 18-21, and/or other computing devices. In some cases, the computing system 17 is part of a cloud computing network. The data channels 16 can be wired lines of a network (e.g., a local area network) and/or wireless channels (e.g., Wi-Fi or cellular network).

Each of the plurality of cameras 18-21 can generate a chronological series of frames (e.g., as images). The plurality of cameras 18-21 can be configured to collect three dimensional information to generate representations of the patient areas 12-15 in three dimensional space. The term camera, as used herein, refers to any device or system of devices configured to optically collect dimensional information. A camera can include one or more sensors configured to register the reception of light in the visible spectrum and/or non-visible spectrum (e.g., along the infrared band). A camera can be a video camera. A camera can comprise one or more laser emitters and one or more laser receivers. In some embodiments, a camera can capture a sequence of frames at a predetermined frame rate, such as six, eight, sixteen, twenty-four, or some other number of frames per second. In some embodiments, a camera can provide infrared illumination or night vision capabilities for operating in low light conditions.

Various camera devices and techniques can be employed to perform a scan of a patient area to collect three dimensional information. Stereoscopic systems and techniques can include the use of two or more cameras viewing the same general area but from different perspectives (e.g., the cameras can be located at different positions). For example, the two cameras may be laterally offset by a few inches. Frames can be simultaneously collected by the cameras and common points between the collected frames can be matched. The frames can then be analyzed to determine which aspects of the two frames are similar to each other and which aspects are not similar to each other. The coordinates of the matching and dissimilar aspects can be determined geometrically (e.g., through triangulation) based on the known offset between the two or more cameras.

A laser based camera system can be used for performing three dimensional scans of a patient area. Such laser based system can have at least one laser and at least one sensor sensitive to reflections of the laser beam. The laser can rapidly scan a laser beam over a scene (e.g., by moving the laser emitter or by moving a mirror, the laser pulsing at discrete points according to a grid) and the sensor can sense reflections of the laser beam reflecting from various features in the scene. The particular direction at which the laser is projected at each moment, and whether an associated reflection was sensed, as well as the time of flight of the laser beam, can be used to build a three dimensional frame of the scene. The time of flight can be calculated from the known time the laser beam was projected and the known time that it was received by the sensor.

Some systems for performing three dimensional scans can include at least one emitter (e.g., laser or infrared based, among other options) and at least one sensor offset from the at least one emitter. Each sensor can be sensitive to the angle at which a reflection of a beam or other projection from the emitter is received after reflecting off of a feature of the scene. The emitter can rapidly scan a scene while the direction and angle of the projection is known at each instance. The angle of reception sensed by the sensor, as well as time of flight, can be determined and the three dimensional coordinates of the reflecting features in the scene can be determined by triangulation or other geometric technique. It is noted that various other techniques for performing three dimensional scans are possible and are contemplated as within the scope of the present disclosure. Various techniques for three dimensional data collection are disclosed in U.S. Patent Application No. 2010/0290698 to Freedman et al., the entirety of which is incorporated herein by reference. While various systems for collecting information in three dimensions are disclosed, embodiments of the present disclosure can be practiced with systems that collect one dimensional information (e.g., a point source sensor) and/or two dimensional information (e.g., a video camera measuring color and light intensity).

Figure 2:
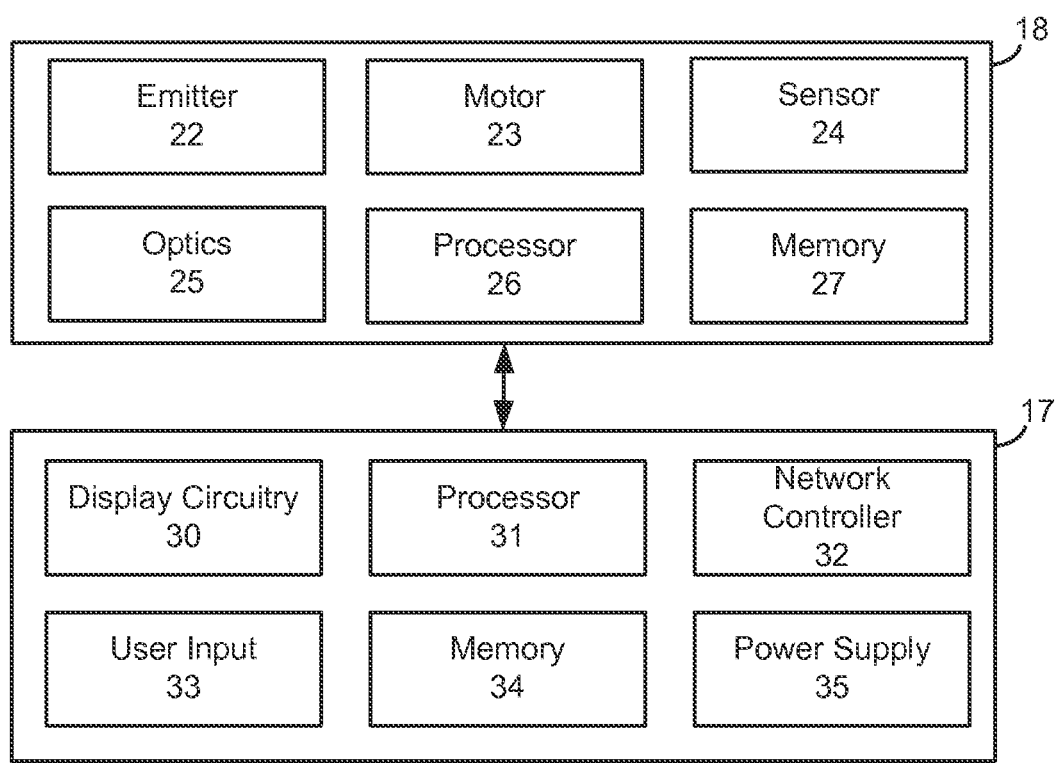
FIG. 2 is a block diagram of components of a monitoring system.

FIG. 2 shows a block diagram of circuitry of the monitoring system 10. Although the particular components of camera 18 are shown as an exemplar, the components of the camera 18 can be included as part of each camera and the monitoring system 10. Also, while the components of camera 18 can be included in one housing, the components may alternatively be part of separate housings, such as separating the emitter 22 and the sensor 24 in different housing that are offset form one another. Furthermore, not all camera embodiments may include each of the components shown in FIG. 2.

The camera can include an emitter 22. The emitter 22 can emit light. The term light, as used herein, refers to electromagnetic radiation. While some wavelengths of light are visible, some other wavelengths that are useful for implementing the systems and method of the current disclosure are not visible. The emitter 22, in various embodiments, can emit visible light, non-visible light, laser light, and any other type of light. Some camera embodiments may not include an emitter 22 and may use, for example, ambient light. In some embodiments, the light, whether emitted by the emitter 22 or ambient, can reflect off of features of the scene and be received by the sensor 24. The sensor 24 can convert the light into electronic signals. The sensor 24 can include a charge-coupled device (CCD) or a complementary metal-oxide-semiconductor (CMOS), among other options.

The camera 18 can include optics 25 for directing and/or receiving light. Optics 25 can include a mirror (e.g., for reflecting a laser), a lens, a filter, and/or other components for sending, capturing, and/or conditioning light. The camera 18 can include a motor 23 for moving one or more components of the camera 18. For example, the motor 23 may be used to scan light over a scene by moving the emitter 22 or a mirror.

The camera 18 can include a processor 26 and memory 27. The processor 26 can perform various computing functions, such as those described herein or otherwise useful for operating the camera 18. The memory 27 can be a non-transient computer readable storage medium (e.g., random access memory or flash) for storing program instructions and/or frames. For example, the processor 26 can be configured to execute program instructions stored on the memory 27 for controlling the camera 18 in scanning a scene with emitted light and converting reflected light into digital signals with the sensor 24, storing the digital signals on the memory 27 as three dimensional frame data, transferring the frame data to the computing system 17, and/or performing any other function. The processor 26 may perform various signal conditioning and/or image processing on the frames. The processor 26 may include a dedicated video processor for image processing. Although not illustrated, the camera 18 can further include a network interface controller and a power supply. The camera 18 may include a user interface which can include user controls and/or an audible alarm.

The computing system 17 can comprise a single housing or multiple housings among which circuitry can be distributed. The computing system 17 can include display circuitry 30 which can provide a graphics output to a screen. Display circuitry 30 can include a graphics processor and graphics memory which can support user interface functionality. Display circuitry 30 may be part of a separate display, such as a screen, handheld device, or remote terminal. Display circuitry 30 can facilitate the display of frames taken by the camera 18 and/or patient status information. User input circuitry 33 can include components for accepting user commands such as a keyboard, mouse, trackball, touchpad, touch screen, joystick, slider bar, or any other control. User input circuitry 33 can facilitate the definition of boundaries and monitoring zones, as will be further described herein.

The computing system 17 can include a processor 31 and memory 34. The memory 34 can be one or more discrete non-transient computer readable storage medium components (e.g., RAM, ROM, NVRAM, EEPROM, and/or FLASH memory) for storing program instructions and/or data. The processor 31 can be configured to execute program instructions stored on the memory 34 to control the computing system 17 in carrying out the functions referenced herein. The processor 31 can comprise multiple discrete processing components to carry out the functions described herein as the processor 31 is not limited to a single processing component. The computing system 17 can include a network controller 32 for facilitating communication with the cameras 18-21 and/or other remote components. The computing system 17 can include a power supply 35 which can facilitate a connection to an electrical outlet and/or the power supply 35 can comprise a battery. Whether distributed or unified, the components of the computing system 17 can be electrically connected to coordinate and share resources to carry out functions.

Figure 3:
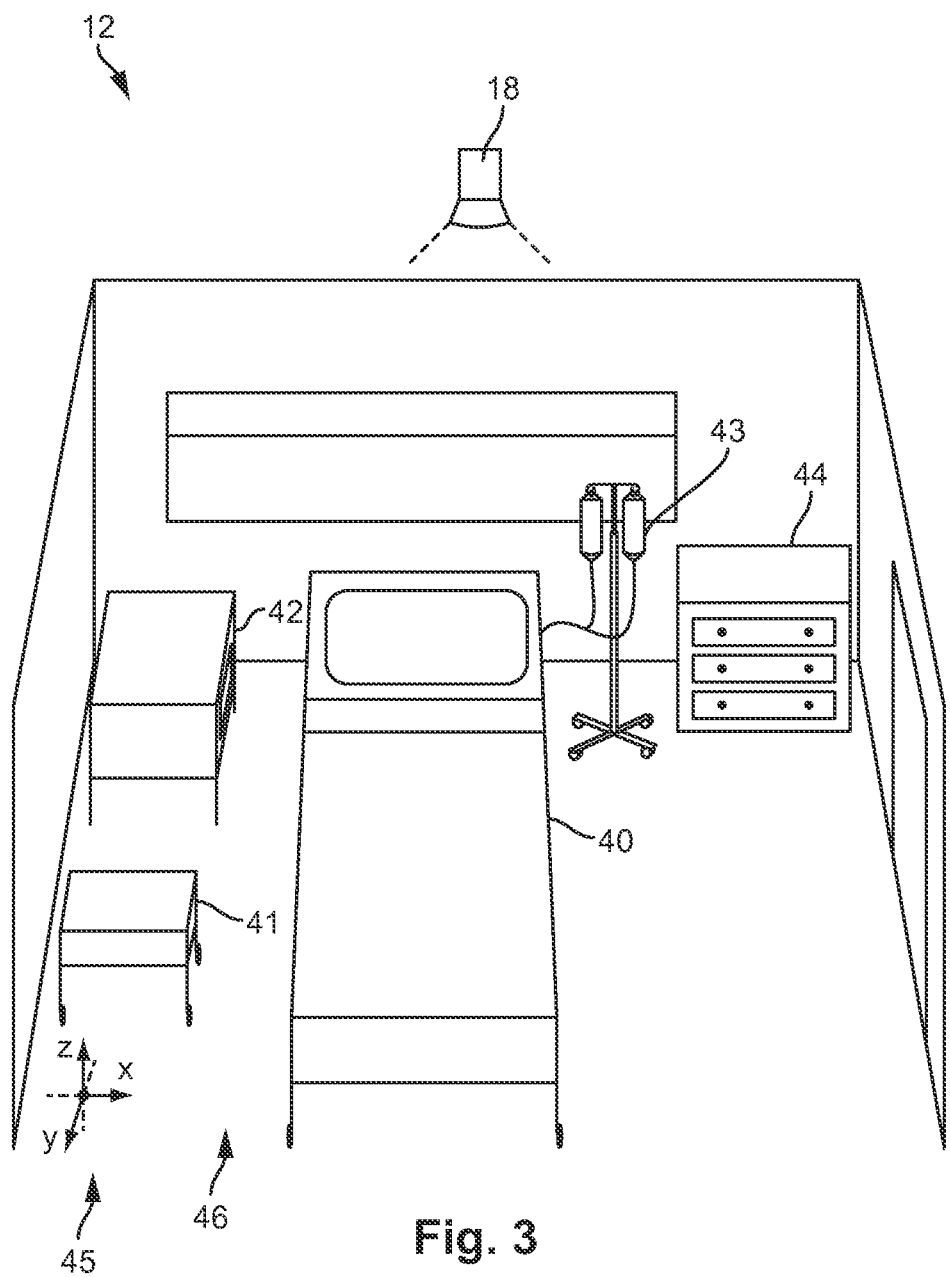
FIG. 3 is a schematic illustration of a patient area which can be monitored by a monitoring system.

FIG. 3 illustrates a schematic view of a patient area 12. The patient area 12 can include a bed 40, cart 41, table 42, intravenous frame 43, and cabinet 44. These objects can represent some of the things commonly found in a patient's room, however it is noted that many other objects can additionally or alternatively be in a patient's room. The camera 18 is shown positioned at the top of the patient's room. The camera 18 can be attached to the ceiling, for example. Elevated camera 18 locations, including but not limited to the ceiling, can be preferred in some implementations so that the camera 18 can view the patient area 12 with minimal obstructions and to view the depth of the room along a vertical axis, as further discussed herein. However, it is noted that cameras of various embodiments can additionally or alternatively be in other non-elevated locations. While the patient area 12 of FIG. 3 corresponds to a hospital room, various other patient areas can be monitored. Likewise, while monitoring the fall risk of a patient from the bed 40 is discussed herein, patients can be monitored in association with other objects and/or risk, such as risks associated with a chair, a wheelchair, a tub, a shower, and/or an entryway, among others.

An axis key 45 is provided in FIG. 3 to facilitate an understanding of how a three dimensional coordinate system could be established in the patient area 12. As shown, the X and Y axes represent lateral coordinates along a horizontal plane (e.g., such as the floor or ceiling) while the Z axis represents vertical coordinates (e.g., height). As shown in FIG. 3, the different features within the patient area 12 can have different locations along the X and Y axes and different heights along the Z axis.

Figure 4:
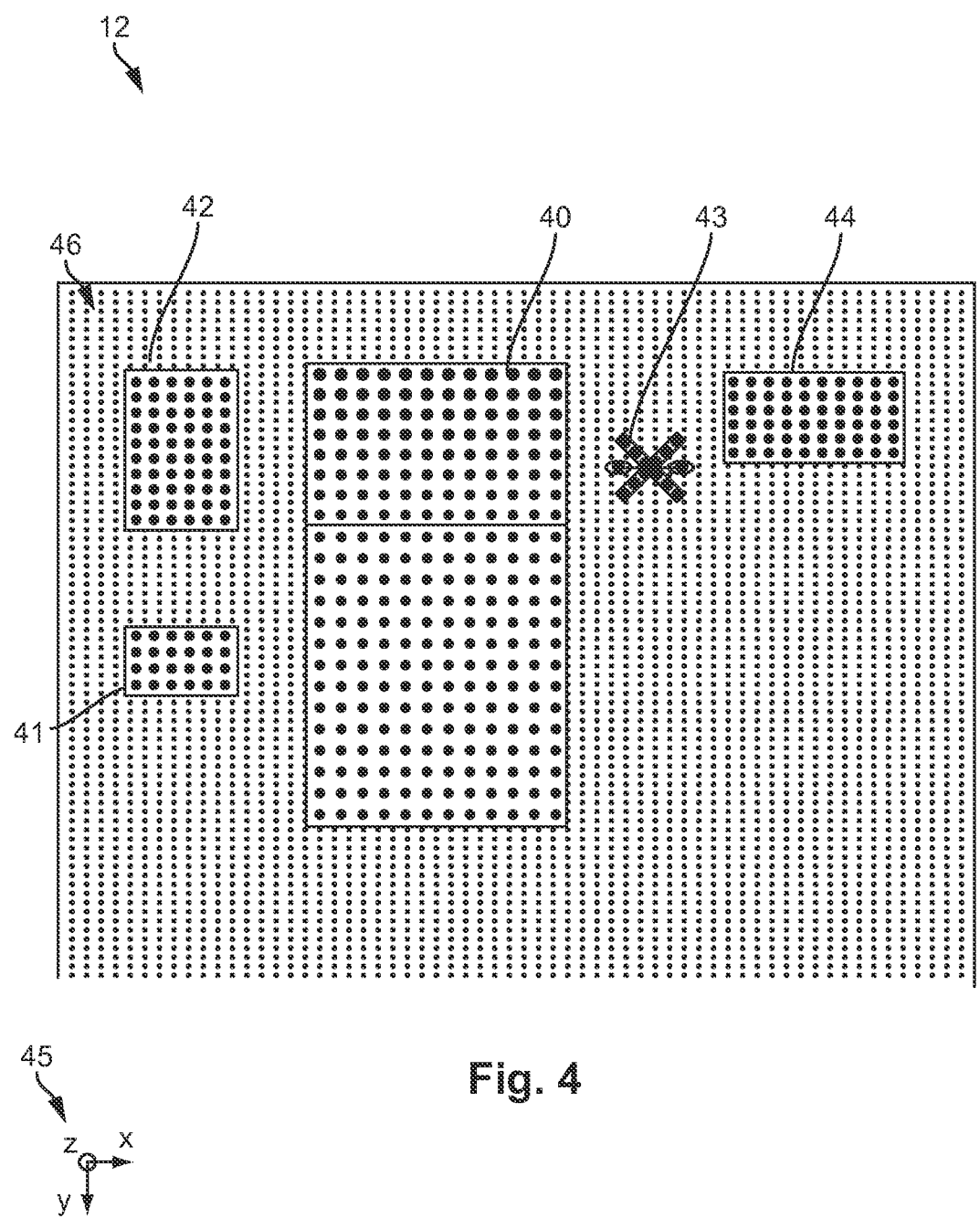
FIG. 4 is a frame of the patient area shown in a pixel grid.

FIG. 4 illustrates a contrived example of a three dimensional scan of the patient area 12 by the camera 18 from FIG. 3. Specifically, FIG. 4 illustrates a point grid reflecting three dimensional information of the patient area 12. A three dimensional scan can include determining the three dimensional coordinates or other spatial relationship of the features of the patient area 12. In the case of the point grid of FIG. 4, light from the emitter 22 can be rapidly pulsed at grid locations of the patient area 12 (e.g., one pulse for each pixel of FIG. 4). The grid pattern can be along the X and Y axes, for example. Whether or not light is sensed by the sensor 24 following each pulse can indicate whether a surface capable of reflecting the light is located at the particular grid location at which the light was just pulsed. Coordinates of features in the patient area 12 can be identified along the X and Y axes. During a scan, a pulse of light can be generated for each square centimeter or other resolution. A pixel of a point grid can be generated for each pulse of light for which reflected light was sensed. The time of flight of a sensed pulse of light can be used to determine the distance from the camera 18 to the reflecting surface. The distance between the camera 18 and the surface can provide a Z axis coordinate for each surface. Other techniques for determining the three dimensional coordinates or other information of a patient area are possible.

Three dimensional coordinates can be represented in various ways. In the point grid of FIG. 4, coordinates along the X and Y axes are represented by the grid position of each pixel and depth along the Z axis is represented by pixel size. For example, the floor 46 of the patient area 12 is generally shown by a background grid of small pixels, the pixels being small because the floor is the furthest distance from the camera 18. The cart 41, table 42, and cabinet 44 are shown with pixels that are larger than the pixels defining the floor 46 because the top surfaces of the cart 41, table 42, and cabinet 44 are closer to the camera 18. The two tallest objects of the patient area 12 are the bed 40 and the intravenous frame 43. The intravenous frame 43 in particular is shown with the largest pixel size because the intravenous frame 43 is the tallest feature in the patient area 12, despite the intravenous frame 43 having a relatively small footprint in the X and Y axes. The bed 40 has pixels of different sizes because the bed 40 has surfaces at different heights. It is noted that the objects of the patient area 12 are shown with borders in FIG. 4 to facilitate an understanding of different pixel sizes and surfaces of particular objects, even though such borders may not be present in all embodiments. In some cases a dimension, such as height, can be indicated with data in 8 bits. For example, height in the patient area can be divided between 0-255 different height levels, with 0 being the lowest (e.g., along the floor 46) and 255 being the closest that the camera 18 can resolve.

It is noted that while multiple objects are present in the patient area 12, only the bed 40 may be relevant to patient monitoring in some cases. For example, some embodiments may determine whether a patient is at increased risk of falling from the bed 40 (e.g., whether the patient is attempting to leave the bed). As such, the other features of the patient area 12 may be irrelevant to patient monitoring or even distracting to a patient monitoring system. Various embodiments of the present disclosure can focus monitoring on the surface of the bed 40 while ignoring other areas of the patient area 12.

Various embodiments of the present disclosure concern monitoring the state of a patient on the bed 40 (or other supporting surface) by determining whether the patient elevates a part of his or her body from the top surface of the bed 40. Such monitoring can be performed by setting one or more height thresholds above the bed 40. Three dimensional monitoring or other techniques can determine whether the patient trips one or more of the thresholds, which can indicate that the patient is attempting to get out of bed or is otherwise at a greater risk of falling from the bed. An alarm can then summon intervention.

It is noted, however, that most patient environments are dynamic environments where the arrangement of the bed 40 is frequently changed. For example, a healthcare professional may perform a blood pressure check or other test, change an intravenous fluid, and/or provide food, each of which can change the position of the bed 40. The cart 41, the bed 40, and the intravenous frame 43 are each wheeled and can be moved around the patient area 12 by health care professionals when attending to a patient. Some of the changes to the patient area 12 can change the position of the bed 40 relative to one or more height thresholds above the bed. For example, the bed 40 is adjustable and the height of different portions of the bed 40 can change over time. Also, patients often have a control for changing the configuration of the bed 40. A height threshold may be too high to intersect with a patient movement, or may be too low and frequently erroneously tripped, if the height threshold is not adjusted to accommodate the change to the bed 40 height. Likewise, a height threshold may be out of position to intersect with patient motion if the threshold is not adjusted following repositioning of the bed 40. As such, various embodiments of the present disclosure concern techniques for dynamically identifying the surface of the bed 40 (or other patient support surface) and setting one or more height thresholds directly above the bed 40 to continuously monitor whether a patient is elevating him or herself from the surface of the bed 40. A monitoring system can continue to monitor the fall risk of a patient despite the bed 40 being moved to a different location, lowered, raised, and/or adjusted over time.

Figure 5:
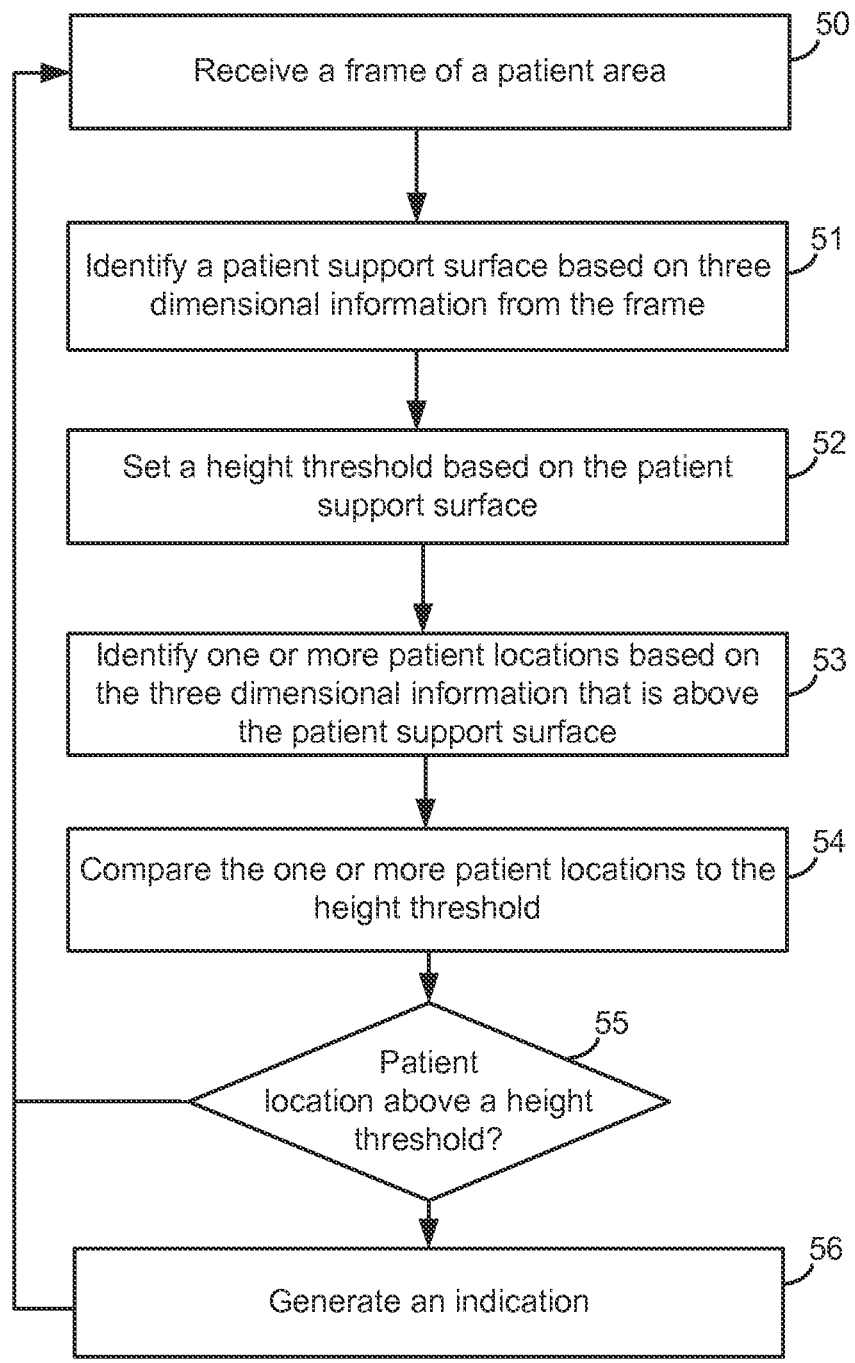
FIG. 5 is a flow chart of a method for monitoring a patient in three dimensions.

FIG. 5 illustrates a method of monitoring a patient using three dimensional information. The method can be implemented by a monitoring system (e.g., as program instructions) as referenced herein. The method of FIG. 5 includes the reception 50 of a frame. A frame, as used herein, can refer to a three dimensional scan or other data representing one or more features of a patient area corresponding to an instant or brief period of time. In some embodiments, the frame can comprise a plurality of pixels defined in a three dimensional coordinate system (e.g., a plurality of pixels defined along X, Y, and Z axes). The three dimensional information can correspond to the point grid of FIG. 4, or other pixels indicative of three dimensional spatial positioning.

The received 50 frame can be part of a chronological series of frames generated by a camera and transmitted to a computing system in sequence, wherein the steps of the method can be performed for the reception 50 of each respective frame of the chronological series. The method steps of FIG. 5 can represent one iteration of a cycle, the cycle being repeated for each frame received 50 in sequence. In some implementations, more than one frame can be received 50 for each iteration of the cycle, wherein each step of the method can be performed based on multiple frames. In some embodiments, each of the steps of the method of FIG. 5 are performed for each frame received 50, while in some other embodiments only some of the steps may be performed upon the reception 50 of each frame while one or more other steps are performed periodically.

Based on the received 50 frame, a patient support surface can be identified 51. The identification 51 of the patient support surface can be automated by a computing system. The patient support surface can correspond to the bed 40 of FIG. 3, or any other object or area on or about which a patient can be monitored. A nominal location of the patient support surface can be identified 51 based on multiple frames. Calculation of a nominal location of the patient support surface is further discussed in connection with the method of FIG. 7. In some embodiments, once a patient support surface is identified 51, a camera can zoom in to particularly focus on the patient support surface to the exclusion of some other areas of the patient area 12. For example, the identified 51 patient support surface can be enlarged within subsequently received 50 frames after the camera focuses on the identified 51 patient support surface. The camera can zoom back out if the patient support surface cannot be identified 51 for subsequent frames and/or a positional change is detected in the patient area 12.

Identification 51 of the patient support surface can include determining the three dimensional coordinates (e.g., along the X, Y, and Z axes) of one or more surfaces of the bed 40. Identification 51 of the patient support surface can include determining the three dimensional coordinates of one or more planes forming the bed 40. Identification 51 of the patient support surface can include identifying one or more boundaries of the patient support surface. A boundary can be detected based on a straight contrast in height (e.g., as compared to the floor 46), which can correspond to an edge of the bed 40. Once a boundary is defined, the patient support surface within the boundary can be identified 51.

Identification 51 of the patient support surface can be performed with the use of a template. The template can be a predetermined set of characteristics of a bed or other patient support surface. Various characteristics that can be used (e.g., as part of a template) to identify 51 a patient support surface include a planar surface, a straight edge, a corner or a set of corners, square shapes (e.g., in the case of a chair), rectangular shapes (e.g., in the case of a bed), size of surfaces (e.g., largest raised surface in the room is often a bed), among others. In some cases, a patient support surface can be identified 51 based in part on the one or more surfaces of the patient support surface not moving for a predetermined period of time (e.g., 5 seconds).

The template can be an image template of the bed 40 or an edge based geometric pattern based on the bed 40, for example. The template can be scaled and/or rotated to attempt to fit the template to the raised pixel patterns of the frame. The template can be used to identify groupings of pixels that are along the same height or along a common plane. The template can be used to identify pixel groupings that outline a square, a rectangle, or other shape. For example, the depth information of the point grid of FIG. 4 can indicate distinct squares and rectangle formed by groups of pixels that are all raised relative to the background (e.g., the floor 46).

Identifying 51 the patient support surface can include identifying multiple planar surfaces. For example, a frame, and the three dimensional information of the frame, can be segmented to find candidate areas that represent surfaces of the patient support surface. The pixels of each segment can be compared to determine whether the pixels match a plane profile. Separate planar surfaces can then be joined by grouping and interpolating. Grouping multiple identified planar surfaces can include determining which non-coplanar surfaces are part of the same bed or other object. For example, intersecting planes can correspond to different parts of an adjustable bed, a chair, or other support structure. Planar surfaces can be determined to intersect in a manner that correspond to a bed, chair, or other structure (e.g., based on a template) and joined to define a single structure. It is noted that planes that evenly intersect are more likely to be part of the same support structure (e.g., planes intersecting at an angle between 0 and 90 degrees) than planes that intersect haphazardly.

Interpolating planar surfaces can be useful where the presence of a patient or object on the bed 40 obscures a portion of the bed 40, such that that multiple planar surfaces are initially separately identified. For example, a patient in the middle of a bed may make the left and right areas of the bed appear as separate planes. Interpolating can including determining which planes are coplanar. Co-planar surfaces that are in proximity to one another (e.g., within the length or width of a bed) can be joined by interpolating between the surfaces to define a larger surface. Interpolating can include interpolating between four corners and/or straight edges determined to be co-planar and separated by less than a predetermined distance.

The method can further include setting 52 a height threshold based on the identified 51 patient support surface. In some cases, the height threshold can be set 52 along the Z axis, or any other axis that measures height. In some cases, the height threshold can be set 52 to correspond to an area a predetermined distance above the identified 51 patient support surface. The predetermined distance can be 2 feet, for example. The area to which the height threshold corresponds may be a planar surface. The height threshold may be a planar surface defined along X and Y axes, and may be tripped by upward motion along the Z axis through the planar surface. The height threshold may be set 52 as a planar surface directly above the identified 51 patient support surface, wherein the planar height threshold is parallel with the patient support surface. The planar height threshold may be set 52 to correspond only to an area directly above the identified 51 patient support surface, such that the planar height threshold does not extend laterally (e.g., along X or Y axes) beyond the identified 51 patient support surface. A height threshold may be set 52 to correspond only to areas that are directly above the surface of the bed 40 and may not be set to correspond to area directly above any of the floor 46, cart 41, table 42, intravenous frame 43, or the cabinet 44.

In some embodiments, multiple height thresholds can be set 52 such that a first height threshold is directly below a second height threshold (e.g., the height thresholds overlap along X and Y axes but are each set 52 at different heights along the Z axis). The multiple thresholds can represent different risk levels for a patient. For example, the first threshold can be set twelve inches above a surface of the bed 40 while the second threshold can be set twenty four inches above the same surface of the bed 40. The second threshold can represent a greater level of fall risk than the first threshold because the patient must rise up beyond the first threshold to trip the second threshold. Different indications can be generated 56 depending on which threshold is tripped. For example, a notification can be issued if the first threshold is tripped while a more urgent alarm can be issued if the second threshold is tripped.

In some embodiments, multiple thresholds can be set 52 above different areas of a patient support surface. For example, a first threshold may be set 52 along a first bed surface while a second threshold may be set 52 along a second bed surface. The first area of the bed can correspond to the foot of the bed while the second area can correspond to the head of the bed. The use of multiple threshold is further discussed in connection with FIG. 6.

The method can further include identifying 53 one or more patient locations based on the three dimensional information that concerns the space above the patient support surface. Identifying 53 the one or more patient locations can include separating pixel information indicative of a patient location from pixel information that is irrelevant to a patient location. In some cases, pixels directly above the identified 51 patient support surface can be assumed to be part of the patient as few other features are likely to be directly above the patient support surface. Separating the pixel information can include separating the pixels that are directly above the patient support surface from pixels in the frame that are not directly above the patient support surface. Separating the pixels can focus a detection algorithm on the space above the bed where the patient is expected to be and can ignore the areas where a patient is not likely to be (or unlikely to fall from). Separating can include distinguishing between those pixels that are directly above the bed from all other pixels of the frame. Pixels directly above the bed can be binned for subsequent analysis. Information concerning pixels that are not directly above the bed can be deleted or disregarded in subsequent analysis. Separating can include only analyzing the three dimensional information for pixels that are directly above the patient support surface to identify 53 a patient location. Only analyzing the three dimensional information for pixels that are directly above the patient support surface can ease some of the computational burden by not analyzing all of the pixel information from each frame. Also, an algorithm that identifies patient features may be more accurate if it only needs to be capable of assessing the relevancy of pixel information found above a patient support surface instead of having to be capable of assessing the relevancy of all of the different pixel features of the frame. For example, a patient identification algorithm may be relatively simple if it only needs to identify surfaces that are above a bed surface (where the surfaces can be assumed to be part of the patient or relevant to the position of the patient since the surfaces are above the bed surface) instead of the algorithm that can discriminate other features found in a patient area whether or not they are located on a bed.

In some embodiments, one or more patient locations can be identified 53 by normalizing the pixels likely associated with the patient. The height of the bed 40 can be different along different areas of the bed. The surface of the bed 40 can be normalized relative to the patient position by subtracting the height of the surface of the bed 40 (i.e. the identified 51 patient support surface) along the different areas from the height of the pixels directly above the same areas. Such normalization can simplify threshold comparison as further discussed herein. For example, the location of each pixel that is directly above the patient support surface can be modified by subtracting a height value from the position information of the pixel. The subtracted height value can be the height (e.g., along the Z axis) of the patient support surface at the same positional location (e.g., along the X and Y axes) as the pixel directly above the patient support surface. The patient support surface is then normalized even if the actual bed surface is curved or bent.

Part or all of the patient can be identified 53 based on a plurality of pixels above the patient support surface being grouped together. Identifying 53 the one or more patient locations can include detecting one or more patient surface outlines based on a pixel grouping. Various three dimensional scanning systems can generate point clouds. A point cloud can include a plurality of pixels grouped together, the group representative of the external surface of an object. Each pixel can have coordinates along X, Y, and Z axes. Surfaces can be interpolated between the pixels within the group to generate a three dimensional model of various objects in a scene.

Each grouping of pixel can be built by associating pixels that are proximate each other. For example, two pixels can be grouped if the two pixels are within a predetermined distance from one another (e.g., measured in three dimensional space). Additional pixels can be added to the grouping if each pixel is within a predetermined distance to at least one pixel of the group, within a predetermined distance to multiple pixels of the group, or within a predetermined distance to all pixels of the group, among other options. Because the patient support surface has been identified 51, clusters of pixels directly above the patient support surface are likely to part of a patient. As such, pixel clusters can be indicative of a feature of a patient. Isolated or otherwise ungrouped pixels can be associated with noise and may not be considered to be part of the patient.

Whether for identifying 51 a patient support surface or identifying 53 one or more patient locations, several techniques can be employed to convert pixel groupings into three dimensional surfaces. Various techniques can include forming a network of triangles over the pixel grouping. Some other techniques can include converting a pixel grouping into a volumetric field and constructing implicit surfaces.

Identifying 53 the one or more patient locations can include detecting pixels associated with the patient generally or detecting particular features of a patient, such as a head, chest, arm, leg, and/or other part. Patterns indicative of particular patient features can emerge by recognizing groupings of pixels in a location where a patient feature would be expected (e.g., the head at the top of the bed, arms as the sides of the bed). Particular features of a patient can be detected with templates that correspond to the particular features of the patient. For example, the template can be applied to groupings of pixels to determine whether the profile of a grouping matches a shape of a head, arm, or other patient feature. Identifying 53 the one or more patient locations can include indentifying separate locations for different features of a patient, such as the respective locations of the patient's head and arms.

The one or more patient locations can be identified 53 based on various detection criteria. In some embodiments, a grouping of pixels that is directly above the patient support surface and in a quantity above a threshold number can be identified 53 to be part of a patient location. For example, a grouping of 3 pixels may not be considered to be part of the patient but a grouping of fifty or more pixels can be identified 53 to be part of a patient location.

In some embodiments, a metric can be calculated based on grouped pixels to identify 53 patient locations. For example, grouped pixels can form three dimensional structures (e.g., the outline of part of a patient). The volumes of the three dimensional structures can be calculated (e.g., as centimeters cubed) and compared to a threshold. If a volume of a group of pixels is larger than the threshold, then the structures can be identified 53 to be a patient location. If the volume is less than the threshold, then the pixels may not be identified 53 to be part of the patient.

While a group of pixels can have a large number of different pixel locations (one location for each pixel), it can be useful to have a single metric to characterize the position of the grouping (e.g., for comparing 54 the pixel grouping indicative of a patient to a height threshold). In some embodiments, a representative metric can be calculated from a grouping of pixels to characterize a position of the grouping. The metric can represent the position or other characteristic of the grouping. For example, if a grouping of pixels is identified 53 to correspond to a head of a patient, then a volume of the grouping, a surface area of the grouping, an elongation of the grouping, a spread of the grouping, a perimeter of the grouping, a geometric center of the grouping, an average height of the pixels of the grouping, or some other metric for characterizing the grouping can be calculated. The representative metric can then be used as a single location or value for representing the pixel grouping, which can simplify tracking of the grouping as further discussed herein.

The method can further include comparing 54 the one or more patient locations to the height threshold. The comparing 54 step can determine whether any part of the patient, or a particular part of the patient (e.g., a head) is at or above the set 52 height threshold. As discussed herein, the lifting of the patient's head or other body part a particular height above the bed can be indicative of an increased fall risk. In some cases, a representative metric for an identified 53 patient location (e.g., a geometric center, average pixel height, volume) can be compared 54 to the threshold. In some embodiments, a minimum volume of a grouping of pixels may be needed to trip the threshold, wherein a grouping of pixel associated with a volume less than the minimum may not trip the threshold.

If one or more of the patient locations are above 55 the height threshold, an indication can be generated 56. Generating 56 the indication can include changing a fall risk status of a patient (e.g., raising the fall risk from low to high), storing a record of the event in memory, and/or issuing an alert (e.g., sounding an alarm perceivable by a healthcare professional and/or an indication on a screen). The cycle of the method can then be repeated with the reception 50 of the next frame of the chronological series. If the one or more patient locations are not above 55 the height threshold in the next iteration, then the fall risk can be lowered and/or an alert can be canceled.

It is noted that the steps of the method of FIG. 5 can be performed in various orders. For example, the steps of the method can be performed in the sequence shown in the flowchart of FIG. 5. However, the steps can be performed in other sequences. Some of the steps can be performed with every iteration of the cycle (e.g., identify 53 the patient location and comparing 54 the location to a height threshold) while some other steps may only be performed periodically (e.g., identifying 51 the patient support surface and/or setting 52 the height threshold). In embodiments where the identification 51 of the patient support surface and/or the setting 52 of the height threshold are only performed periodically (e.g., with every 5 frame received, once every 10 seconds), a nominal location of the patient support surface can be used each cycle and then updated periodically, as further discussed herein. In some embodiments, the identification 51 of the patient support surface and/or the setting 52 of the height threshold can be performed based on the occurrence of an event, such as a detected change in illumination of the patient area. The change in illumination of the patient area can indicate a rearranging of the objects in the patient area. In some embodiments, the identification 51 of the patient support surface and/or the setting 52 of the height threshold can be performed based on a patient location being above 55 a height threshold or other indicator of an increased fall risk.

Figure 6:
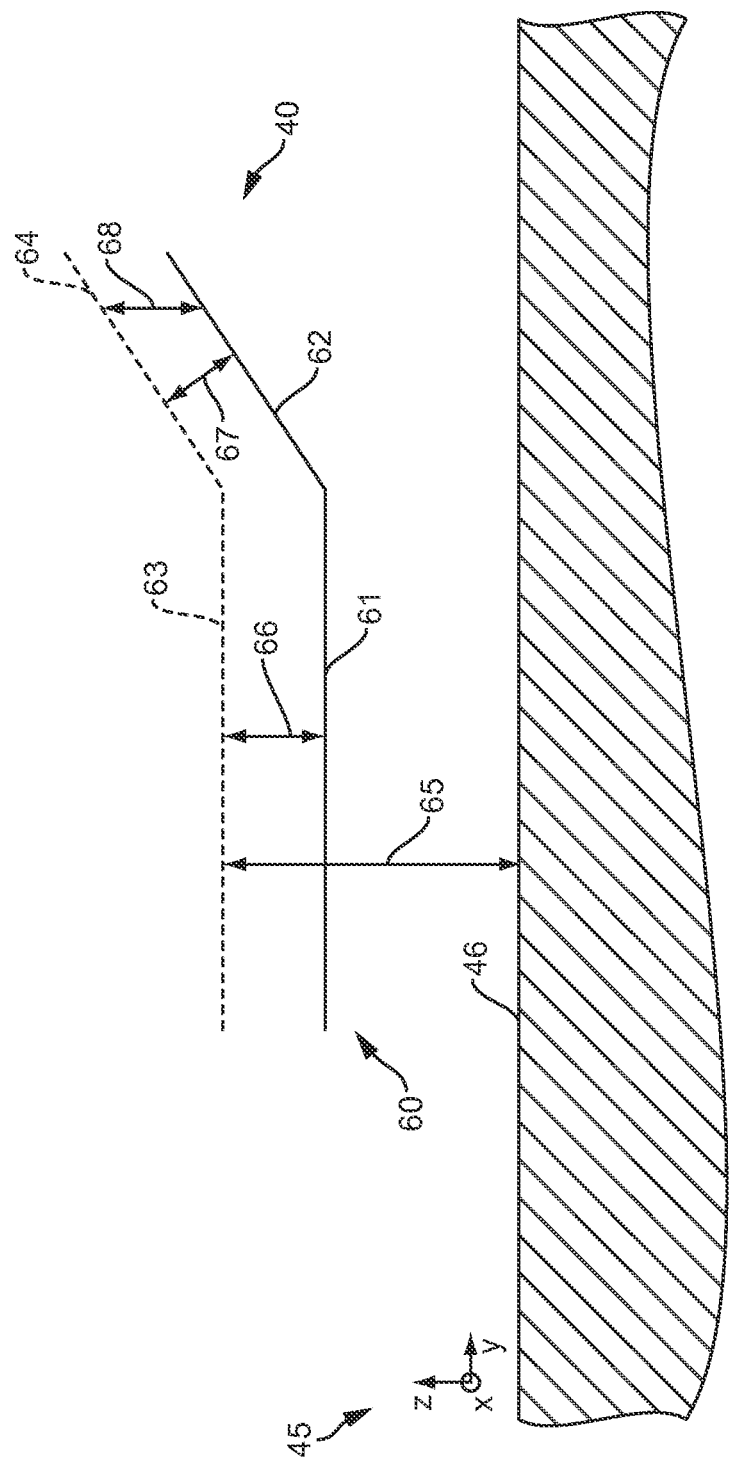
FIG. 6 is a schematic side view of a bed in association with multiple height thresholds.

FIG. 6 illustrates a schematic diagram of height thresholds above a patient support surface 60. Specifically, FIG. 6 shows how multiple thresholds can be set above different portions of a patient support surface 60. The patient support surface can be identified 51, and the height thresholds set 52, according to the techniques of FIG. 5, for example. The patient support surface 60 can correspond to the bed 40. The patient support surface 60 can comprise a first patient support surface 61 and a second patient support surface 62. The first patient support surface 61 can represent the lower half, or foot, of the bed 40. The second patient support surface 62 can represent the upper half, or head, of the bed 40.

A first height threshold 63 can be set directly above the first patient support surface 61. A second height threshold 64 can be set directly above the second patient support surface 62. The first height threshold 63 can be set a first distance 66 above the first patient support surface 61. The second height threshold 64 can be set a second distance 68 above the second patient support surface 62. In some embodiments, the first distance 66 can be different from the second distance 68. In some cases, the second height threshold 64 can be separated from the second patient support surface 62 by a third distance 67 measured along an axis orthogonal to both of the planes of the second height threshold 64 and the second patient support surface 62. In some cases, the first height threshold 63 can be set based on a fourth distance 65 to the floor 46. Various other distances and threshold arrangements are possible.

While FIG. 6 shows the patient support surface 60, the first height threshold 63, and the second height threshold 64 in a two dimensional side view, it is noted that the first height threshold 63 can be a plane that is parallel with the plane of the first patient support surface 61. The plane of the first height threshold 63 can fully or partially overlap with the plane of the first patient support surface 61. For example, the first height threshold 63 can cover the same area (e.g., along the X and Y axes) as the first patient support surface 61 but can be separated from the first height threshold 63 by a first distance 66. Likewise, the second height threshold 64 can cover the same area (e.g., along the X and Y axis) as the second patient support surface 62 but can be separated from the second height threshold 64 by a second distance 68. In this way, the plane of the first height threshold 63 and the second height threshold 64 (or a single height threshold) can have the same length and width as the patient support surface 60 such that the plane of the first height threshold 63 and the second height threshold 64 is laterally matched directly above the patient support surface 60 or otherwise does not extend laterally beyond the sides of the patient support surface 60. Alternatively, the plane of the first height threshold 63 and the second height threshold 64 (or the single height threshold) can have a shorter length and/or width than the patient support surface 60 such that the plane of the first height threshold 63 and the second height threshold 64 does not extend to the sides of the patient support surface 60. In another embodiment, the plane of the first height threshold 63 and the second height threshold 64 (or the single height threshold) can have a longer length and/or width than the patient support surface 60 such that the plane of the first height threshold 63 and the second height threshold 64 extends laterally beyond the sides of the patient support surface 60 to cover a larger area than the footprint of the patient support surface 60.

In some cases, a computing system can take different steps depending on whether the one or more patient locations are above the first height threshold 63 and/or the second height threshold 64. The first distance 66 can be different from the second distance 68 to account for differences in relevant patient activity over the different patient support surfaces. For example, a patient may frequently lift his or her hear off of the bed 40 but not attempt to get up. However, a patient may rarely raise a foot or leg without attempting to get closer to an edge of the bed 40 (e.g., when getting out of the bed 40 or shifting positions). The raising of the head may only sometimes be a precursor to a patient attempting to get out of the bed 40, while the raising of a knee may be a more reliable indicator that the patient is attempting to get out of the bed 40 or otherwise that the patient is at a greater risk of falling. The higher second height threshold 64 along the head of the bed 40 can be useful to accommodate the patient putting a hand up or slightly raising his or her head without generating an indication 56 while the patient raising a leg might be an infrequent but more sensitive indicator that the patient is moving and at risk of falling. The first height threshold 63 may be relatively closer to the lower patient support surface 61 to be more sensitive to reliable leg motion while the second height threshold 64 may be relatively farther from the second patient support surface 62 to be less sensitive to less predictable head motions. In some cases, the tripping of the second height threshold 64 may raise a fall risk status to a greater degree than the tripping of the first height threshold

63. For example, tripping the first height threshold 63 may generate a more urgent warning than the tripping of the second height threshold 64.

Various embodiments of the present disclosure can employ one or more buffers when monitoring a patient. The method of FIG. 7 outlines ways in which one or more buffers can be used in patient monitoring. A buffer can comprise one or more memory structures. Multiple buffers can share a common memory structure. A buffer of the present disclosure can operate on a first-in first-out basis. The method could be performed by a computing system as described herein. The method of FIG. 7 can refer to the same embodiment of the method of FIG. 5, wherein the flowcharts highlight different aspects of the method. Alternatively, the method of FIG. 7 can be implemented separately from the method of FIG. 5.

Figure 7:
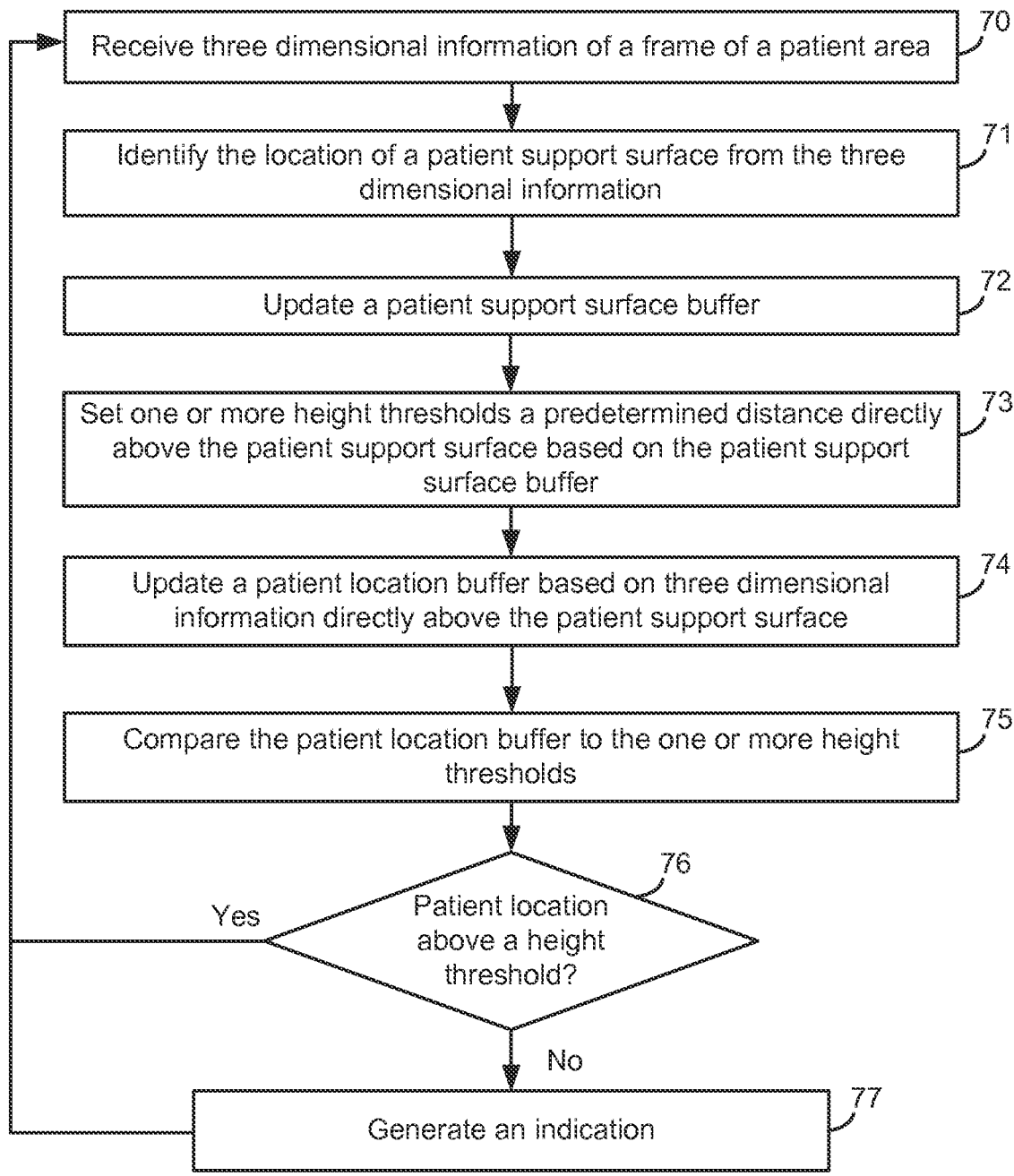
FIG. 7 is another flow chart of a method for monitoring a patient in three dimensions.

The method of FIG. 7 includes receiving 70 three dimensional information of a frame of a patient area. The reception 70 step can be performed in various ways described herein, including as described in connection with the method of FIG. 5. The received 70 three dimensional information can include receiving a whole frame, receiving pixel information (e.g., pixel coordinates), and/or any information that can be used in patient monitoring. The method can further including identifying 71 the location of a patient support surface from the three dimensional information. The location of the patient support surface can be identified 71 using any technique referenced herein, including by use of a template.

A patient support surface buffer can be updated 72 based on the identified 71 location of the patient support surface. The buffer can contain coordinate information for each pixel that defines or is otherwise associated with the patient support surface. Information concerning the location of the patient support surface can be stored in the patient support surface buffer. In particular, information concerning the location of the patient support surface from different received 70 frames (e.g., the sequential frames of a chronological series of frames) can be stored together in the buffer. In some embodiments, information concerning the identified 71 location of the patient support surface for each of N number (e.g., N=32) of frames can be stored in the buffer. The N number of frames can be a chronological series, such that the patient support surface buffer stores N number of identified 71 locations of the patient support surface of the N number of most recently received 70 frames.

The building up of frames over time can facilitate the calculation of a nominal location of the patient support surface. Updating 72 the patient support surface buffer can include calculating the nominal location of the patient support surface based on the frame information collected in the patient support surface buffer, as further described herein. As such, the nominal location of the patient support surface can be calculated from information of a plurality of frames received 70 over time. The use of the patient support surface buffer can correct for errors and smooth changes in the location of the patient support surface and/or the camera. For example, a person moving in a room can temporarily obscure a bed when one or more three dimensional scans are being conducted. A change in illumination within the room can disrupt a scan or confuse a sensor. Other sources of noise can also be present. In any case, the use of a patient support surface buffer can allow the patient monitoring system to handle temporary disruptions in data collection while maintaining a location of a patient support surface.

In some cases, a nominal patient support location can be calculated based on the three dimensional information collected in the patient support surface buffer. For example, a mean position (e.g., along X, Y, and/or Z axes), standard deviation, and/or other aggregation can be calculated for each pixel over the plurality of frames. In some cases, a high standard deviation or other variation of a particular pixel location over the plurality of frames can indicate that the pixel is not part of the bed or other patient support surface. The pixel can be marked as not part of the patient support surface and not used in subsequent patient support surface location calculations. The pixel can be deleted from the buffer. In some embodiments, pixels that are greater than a predetermined distance above the nominal location of the patient support surface can be marked as not part of the patient support surface. Filtering techniques, such as a wide kernel Sobel filter, can be used on the three dimensional information to determine whether an area has a uneven height, which can correspond to a bend in the patient support surface, a point at which the body of a patient touches the bed, or other feature. Such pixels, identified by the filter, can be marked as not being part of the patient support surface. In any case, one or more planar surfaces can be identified and grouped as discussed herein. Pixels that fit a template characteristic of a patient support surface (e.g., a template for the bed 40) as averaged or consistently over the plurality of frames can be marked to, or otherwise be considered to, represent a nominal location of the patient support surface (e.g., a nominal bed surface). The nominal location of the patient support surface can be used as the identified patient support surface.

Updating 72 a patient support surface buffer can include adding the identified 71 location of the patient support surface from the most recently received 70 frame to the patient support surface buffer. In some cases, a location of the patient support surface can be calculated based on the pixel information from each of the frames in the patient support surface buffer. The calculated location can be, for example, aggregated from each identified 71 patient support surface location from a plurality of frames received 70 over time. In some cases, updating 72 the patient support surface buffer can include recalculating the location of the patient support surface based on the information within the buffer, including the most recently identified 71 location of the patient support surface.

The nominal location of the patient support surface can be recalculated (e.g., as part of each update 72) for each subsequently received 70 frame. In some cases, the three dimensional information of the next frame can be added to the patient support surface buffer. The three dimensional information of the oldest frame can be removed from the patient support surface buffer. The nominal location of the patient support surface can then be recalculated from the information in the buffer. Alternatively, a nominal location of the patient support surface can be incrementally changed based on the reception 70 of each new frame. For example, the location of the patient support surface can be identified 71 in the next frame. A comparison (e.g., by subtraction) can be performed between the newly identified 71 location of the patient support surface and the nominal location of the patient support surface. Adjustments can be made to particular pixel locations that are less than a threshold difference between the newly identified 71 location of the patient support surface and the nominal location of the patient support surface. Pixel locations that are greater than the threshold can be ignored as noise and the nominal location of the patient support surface can be unchanged (by that pixel location).

The method can further include setting 73 one or more height thresholds a predetermined distance directly above the patient support surface based on the patient support surface buffer. Various options for setting a height threshold are discussed herein (e.g., in connection with FIG. 5). Setting 73 the one or more height thresholds can include setting 73 the one or more height thresholds directly above one or more planar surfaces of the patient support surface. As discussed above, a location of patient support surface can be calculated from all of the identified 71 locations of the patient support surfaces from the patient support surface buffer (e.g., over 32 frames) as a nominal location of the patient support surface. The one or more height thresholds can be set based on the aggregated location from all of the identified 71 locations of the patient support surface buffer. For example, the one or more height thresholds can be set 73 based on the nominal location of the patient support surface.

The method can further include updating 74 a patient location buffer based on three dimensional information concerning the space directly above the patient support surface. The patient location buffer can be any type of memory structure referenced herein. The patient location buffer can contain information concerning the location of one or more features of a patient on the patient support surface from a plurality of frames. The patient location information in the patient location buffer can be from the same frames as the location information within the patient support surface buffer. Alternatively, the patient location information in the patient location buffer can be limited to three dimensional information concerning the space directly above the patient support surface, and may not include three dimensional information concerning areas other than the space directly above the patient support surface.

In some embodiments, identification of a location of one or more features of a patient can be performed based on the three dimensional information concerning space directly above the patient support surface based on the most recently received 70 frame, and the one or more locations can be added to the patient location buffer in the update 74, wherein the patient location buffer contains the locations of the patient (e.g., locations of particular parts of the patient) identified for each of a plurality of frames. The locations can be averaged or in some manner aggregated to determine the aggregate location of part or all of the patient. Alternatively, the update 74 can include adding the three dimensional information concerning the space directly above the patient support surface to the patient location buffer, wherein the patient location buffer can contain all of the three dimensional information concerning the space directly above the patient support surface for each of a plurality of previously received 70 frames. In this manner, the buffer can contain raw data concerning the space directly above the patient support surface to the exclusion of data concerning space not directly above the patient support surface. The location of the patient can then be determined based on the data within the patient location buffer. A nominal patient location can be calculated from the three dimensional information concerning the space directly above the patient support surface using a similar technique as calculating and/or updated a nominal location of the patient support surface.

The method can further include comparing 75 the location of the patient to the one or more height thresholds. The comparison can be performed according to any technique referenced herein. The comparing 75 step can determine whether any part of the patient, or a particular part of the patient (e.g., a head) is at or above a set 73 height threshold. If one or more of the patient locations are above 76 the height threshold, an indication can be generated 77. Generating 77 the indication can include changing a fall risk status of a patient (e.g., raising the fall risk from low to high), and/or issuing an alert (e.g., sounding an alarm or providing a notification on a screen). The cycle can then be repeated with the reception 70 of the next frame of the chronological series.

Figure 8A:
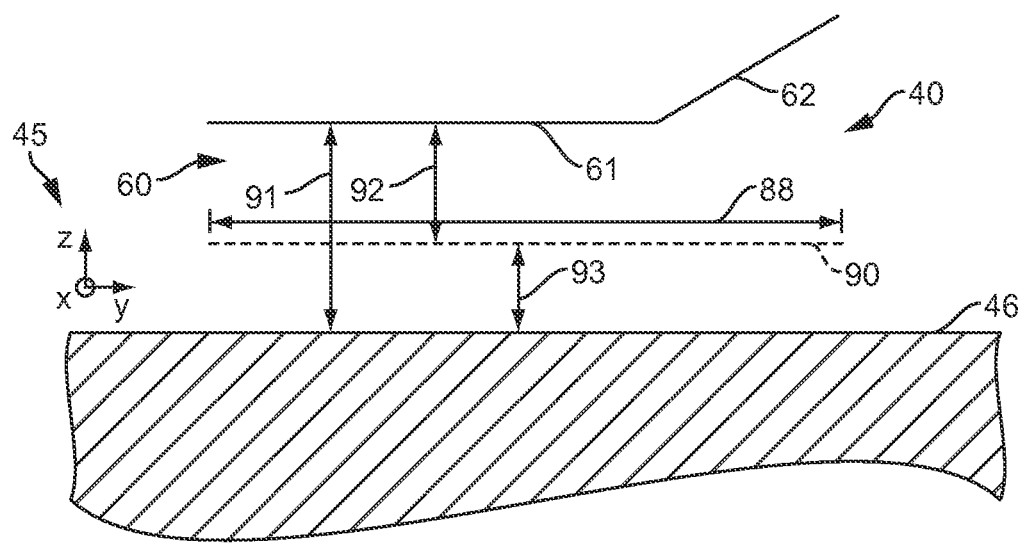
FIGS. 8A-B are schematic illustrations of a patient area which can be monitored by a monitoring system using lower thresholds.
Figure 8B:
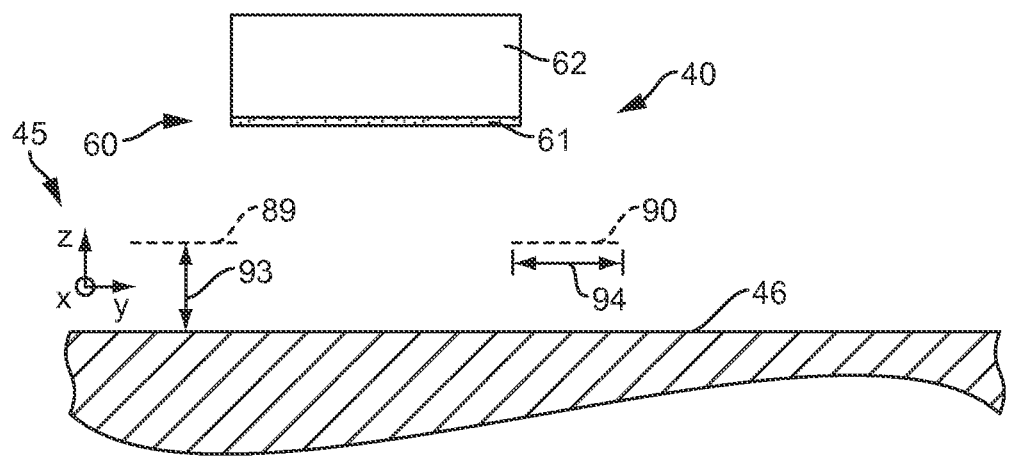

While setting a threshold directly above a bed surface has been used as an exemplary embodiment herein, the techniques of the present disclosure can be applied to setting other thresholds for patient monitoring. FIGS. 8A-B illustrate schematic diagrams of lower thresholds below a patient support surface 60. Specifically, FIG. 8A is a side view of the patient support surface 60 and shows a first lower threshold 90 below the patient support surface 60. FIG. 8B is a front view of the patient support surface 60 and shows the first lower threshold 90 and a second lower threshold 89. The first lower threshold 90 and the second lower threshold 89 can be used to detect a patient's foot or other object dropping below the plane of the patient support surface 60 indicative of a patient exiting the bed 40, as further discussed herein. The first lower threshold 90 and the second lower threshold 89 can be laterally offset from the footprint of the patient support surface 60.

The patient support surface 60 of FIGS. 8A-B can be the same bed 40 referenced elsewhere herein (e.g., that of FIGS. 3, 4, and 6) and can be identified using any technique referenced herein (e.g., in accordance with the methods of FIGS. 5-6 and 10-11). Additionally, in some embodiments the floor 46 surface can be identified using any of the techniques used herein for identifying a surface, such as any technique disclosed herein for identifying a patient support surface. Criteria for identifying the floor 46 can include the planar surface in a frame with the lowest height along the Z-axis, for example. Based on the identification of the patient support surface 60 and/or the floor 46, one or more lower thresholds can be set.

A lower threshold can be set as a two dimensional plane at a height that is lower than the patient support surface 60 and higher than the floor 46. As shown in FIG. 8A, the first threshold 90 can be set at a height that is a predetermined distance 92 below the patient support surface 60. The predetermined distance 92 can be twelve inches, for example, however other distances are contemplated. The predetermined distance 92 can be a predetermined number of pixels. The first threshold 90 can be set at a height that is a predetermined distance 93 above the floor 46. The predetermined distance 93 can be twelve inches, for example, however other distances are contemplated. The predetermined distance 93 can be a predetermined number of pixels. The first threshold 90 can be set at a height that is a predetermined ratio of the height 91 of the patient support surface 60. For example, the first threshold 90 can be set at a height that is ½ or ⅔ of the height 91 of the patient support surface 60. In some cases, the first threshold 90 can be set at a height that is level with the patient support surface 60. In this way, the first threshold 90 can be set to be co-planar with the patient support surface 60. While the first lower threshold 90 is shown to be a consistent height in FIG. 8A (i.e. parallel with the X-Y plane), the height of the first lower threshold 90 can be different for different sections of the first lower threshold 90. For example, if the height of the first lower threshold 90 were to be set based on the height of the patient support surface 60, then a first portion of the first lower threshold 90 can be set to correspond to the consistent height of the first patient support surface 61 while a second portion of the first lower threshold 90 can be set to incline parallel with the second patient support surface 62. In some embodiments where the first lower threshold 90 is set based on the height of the patient support surface 60, the first lower threshold 90 can be set based on the lowest height of the patient support surface 60 and/or the average height of the patient support surface 60, for example. It is noted that any lower threshold can be set at any height as discussed herein. For example, the second lower threshold 89 can be set at the same height, or in the same manner, as the first threshold 90.

Setting a lower threshold can include setting the lower threshold to have a length and a width. A length dimension can correspond to the Y-axis extending along the long dimension of the bed 40 while width can correspond to the X-axis extending along the short dimension of the bed 40. A lower threshold can extend along the entire floor 46. However, to avoid false alarms, it may be useful to limit the lateral extent along the X-axis and the Y-axis of a lower threshold. As shown, the first lower threshold 90 has a length 88. The length 88 can be set based on the length of the patient support surface 60. For example, the length 88 of the first lower threshold 90 can be set to be the same length of the patient support surface 60. In some other embodiments, the length 88 of the first lower threshold 90 can be set to be shorter or longer than the length of the patient support surface 60 by some predetermined factor. The length of any threshold referenced herein, such as the first height threshold 63, can be set as described above (e.g., the length of the first height threshold 63 can be set based on the length of the patient support surface 60, such as to match the length of the patient support surface 60).

The width 94 of the first lower threshold 90 can be set in various ways. In some cases, the width 94 is a predetermined distance, such as twelve inches, however other widths are contemplated. In some cases, the width 94 is a predetermined number of pixels. An inner edge of the first lower threshold 90 can be set aligned with an outer edge of the patient support surface 60. For example, an inner edge (closest to the patient support surface 60) of the first lower threshold 90 can be set directly below the outer edge of the patient support surface 60. As shown in FIG. 8B, each of the first lower threshold 90 and the second lower threshold 89 extend laterally away from the lateral edges of the patient support surface 60. In some embodiments, the first lower threshold 90 and the second lower threshold 89 are not set to be directly below the patient support surface 60, but are set to be adjacent to the lateral sides of the patient support surface 60. A lower threshold can additionally or alternatively be set along the foot or head of the patient support surface 60 in the same manner as the first lower threshold 90.

One or more patient locations can be compared to the first lower threshold 90 and the second lower threshold 89 to determine whether any part of the patient traverses either threshold. Such monitoring can be conducting in any manner referenced herein, such as described in association with FIGS. 5-6 and 10-11. However, unlike with some previous embodiments, the analysis of the patient locations is not limited to the space directly above the patient support surface 60 when monitoring the first lower threshold 90 and the second lower threshold 89. For example, patient locations can be identified based on three dimensional information that is above the floor 46 when monitoring the first lower threshold 90 and the second lower threshold 89. In some embodiments, the patient locations can be detected by limiting the patient location analysis to the three dimensional information that is directly above any of the first lower threshold 90, the second lower threshold 89, or the patient support surface 60 (and/or directly above any other lower threshold).

An indication can be generated if a patient location traverses a lower threshold. Such indication can be any indication referenced herein, including changing a status of the patient and/or issuing an alert. Such status or alert may specifically identify that a lower threshold has been traversed and/or that the patient is exiting the bed 40.

Figure 9A:
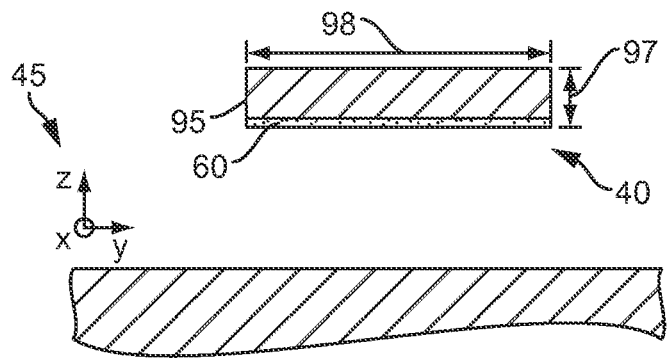
FIGS. 9A-B are schematic illustrations of a patient area which can be monitored by a monitoring system using vertical thresholds.
Figure 9B:
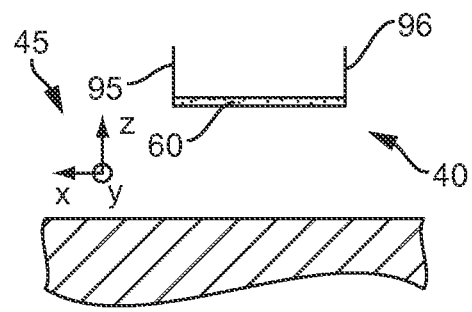

While setting a planar thresholds parallel with a patient support surface have been used as an exemplary embodiment herein (e.g., in the case of height and lower thresholds), the techniques of the present disclosure can be applied to setting other thresholds for patient monitoring. FIGS. 9A-B illustrate schematic diagrams of vertical thresholds on the lateral sides of a patient support surface 60. Specifically, FIG. 9A is a side view of the patient support surface 60 and shows a first vertical threshold 95 extending vertically from a lateral side of the patient support surface 60. FIG. 9B is a front view of the patient support surface 60 and shows the first vertical threshold 95 and a second vertical threshold 96. The patient support surface 60 of FIGS. 9A-B can be the same bed 40 referenced elsewhere herein and can be identified using any technique referenced herein (e.g., in accordance with the methods of FIGS. 5-6 and 10-11). It is noted that while the patient support surface 60 has been shown elsewhere herein having the inclined portion of an adjustable bed, the patient support surface 60 is shown as flat in FIGS. 9A-B for the sake of simplicity. The first vertical threshold 95 and a second vertical threshold 96 can be used to detect a part of a patient approaching or extending over an edge of the bed 40, as further discussed herein.

The first vertical threshold 95 and the second vertical threshold 96 can be set using any technique for setting a threshold referenced herein, yet adapted for a vertical orientation. Each vertical threshold can correspond to a respective vertical plane extending upward from a respective one of a plurality edges of the patient support surface 60 (e.g., the left and right edges). Each respective vertical plane can extend a predetermined distance above the patient support surface, measured in inches or pixels, for example. Each respective vertical plane can have a length equal to a length of the patient support surface. Each of the first vertical threshold 95 and the second vertical threshold 96 can be a plane that is orthogonal to the patient support surface 60. It is noted that a vertical threshold does not necessarily have to extend straight up (e.g., parallel with the Z-axis), and thus can include slanted planes that extend along with Z-axis. Each of the first vertical threshold 95 and the second vertical threshold 96 can be a plane that is orthogonal to the patient support surface 60. Each of the first vertical threshold 95 and the second vertical threshold 96 can have a lower side that intersects with, or is adjacent to, a lateral side of the patient support surface 60.

Each of the first vertical threshold 95 and the second vertical threshold 96 can then extend vertically from its respective lower side (e.g., proximate the patient support surface 60) to an upper side (e.g., distal of the patient support surface 60). This distance between the lower side and the upper side can correspond to the height 97 of each vertical threshold. The height 97 can be a predetermined distance (e.g., one or two feet) or a predetermined number of pixels. It is noted that the patient support surface 60 of FIGS. 9A-B is flat, and as such the distance from the top of the vertical thresholds 95 and 96 to the patient support surface 60 does not change. However, in the case of an included bed or an otherwise uneven patient support surface 60, the first vertical threshold 95 and the second vertical threshold 96 can be set to match the changes in height of the patient support surface 60 by also changing in height such that the height 97 of the first vertical threshold 95 and the second vertical threshold 96 are consistent along the length 98 of the patient support surface 60. It is noted that the first vertical threshold 95 and the second vertical threshold 96 having the height 97 allows monitoring at different heights. For example, if the height 97 is two feet, then lateral movement of the patient off of the patient support surface 60 can be detected whether the movements are 1 inch from the patient support surface 60 or twelve inches from the patient support surface 60.

Each of the first vertical threshold 95 and the second vertical threshold 96 can also have a length 98. The length 98 can be set based on the length of the patient support surface 60. For example, the length 98 of either of the first vertical threshold 95 or the second vertical threshold 96 can be set to be the same length as the patient support surface 60. In some other embodiments, the length 98 of the first vertical threshold 95 or the second vertical threshold 96 can be set to be shorter or longer than the length of the patient support surface 60 by some predetermined factor.

One or more patient locations can be compared to the first vertical threshold 95 and the second vertical threshold 96 to determine whether any part of the patient traverses either threshold. Such monitoring can be conducting in any manner referenced herein, such as described in association with FIGS. 5-6 and 10-11. However, unlike with some previous embodiments, the analysis of the patient locations may not limited to the space directly above the patient support surface 60 when monitoring the first vertical threshold 95 and the second vertical threshold 96. For example, patient locations can be identified based on three dimensional information that is above the floor 46 when monitoring the first vertical threshold 95 and the second vertical threshold 96. In some embodiments, the analysis of the patient locations may be limited to the space above the patient support surface 60 when monitoring the first vertical threshold 95 and the second vertical threshold 96.

An indication can be generated if a patient location traverses either of the first vertical threshold 95 or the second vertical threshold 96. Such indication can be any indication referenced herein, including changing a status of the patient and/or issuing an alert. Such status or alert may specifically identify that a vertical threshold has been traversed and/or that the patient is exiting the bed 40.

It is noted that while various different thresholds have been discussed in separate embodiments, any of the thresholds can be utilized in the same embodiment. For example, one or more of the first height threshold 63, the second height threshold 64, the first lower threshold 90, the second lower threshold 89, the first vertical threshold 95, and the second vertical threshold 96 can be set and monitored in association with the patient support surface 60 as described herein. Similar or different indications can be generated based on which of the thresholds is traversed.

Figure 10:
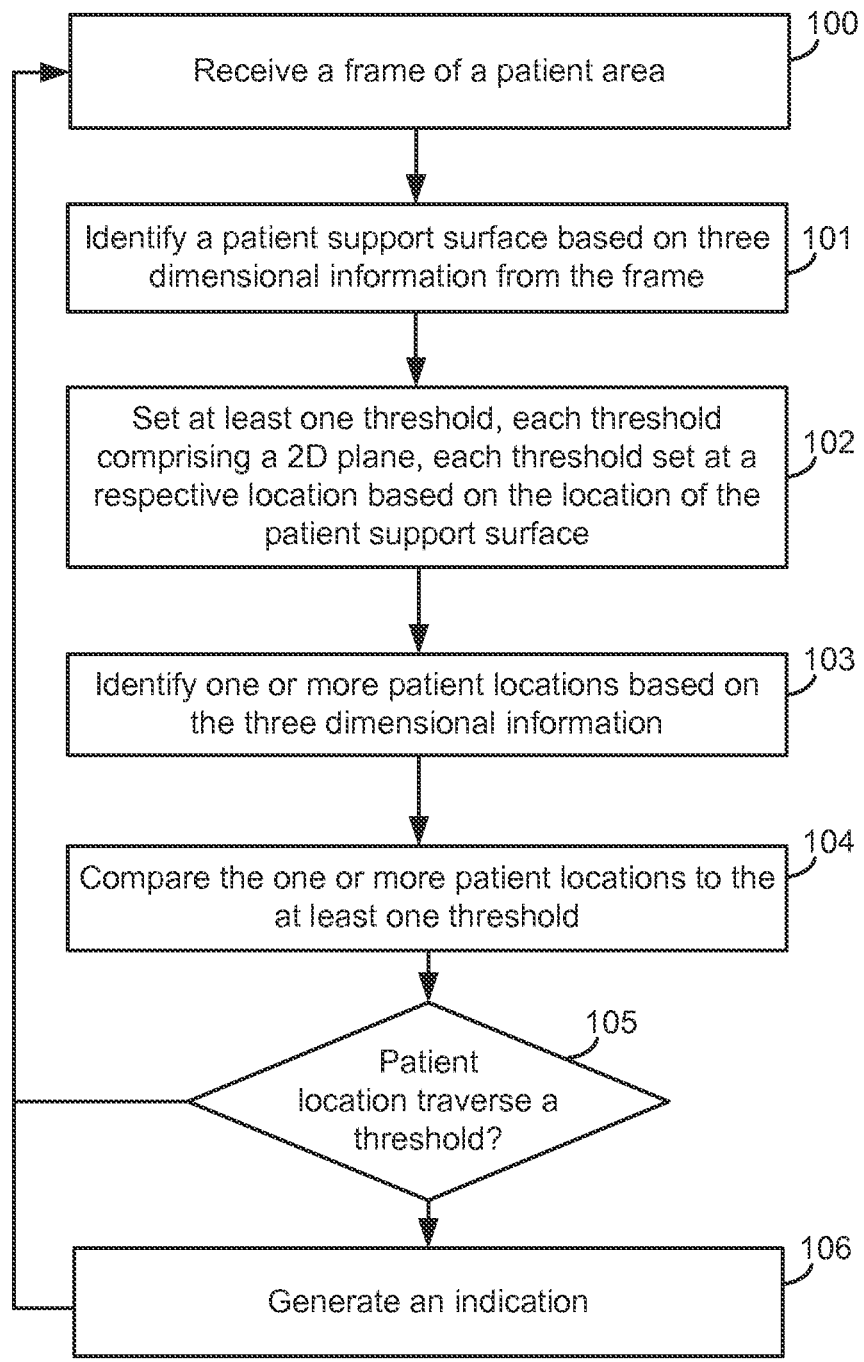
FIG. 10 is another flow chart of a method for monitoring a patient in three dimensions.

FIG. 10 illustrates a method of monitoring a patient using three dimensional information. The method can be implemented by a monitoring system (e.g., as program instructions) as referenced herein. It is noted that the method of FIG. 10 is similar to the methods of FIGS. 5-6 with the difference that FIG. 10 is directed to establishing various type of thresholds (e.g., height thresholds, lower thresholds, and vertical thresholds) while the methods of FIGS. 5-6 focus on establishing height thresholds. Any of the techniques referenced in connection with the methods of FIGS. 5-6 can be applied to the method of FIG. 10.

The method of FIG. 10 includes the reception 100 of a frame. The frame can comprise a plurality of pixels defined in a three dimensional coordinate system (e.g., a plurality of pixels defined along X, Y, and Z axes). The three dimensional information can correspond to the point grid of FIG. 4, or other pixels indicative of three dimensional spatial positioning. The received 100 frame can be part of a chronological series of frames generated by a camera and transmitted to a computing system in sequence, wherein the steps of the method can be performed for the reception 100 of each respective frame of the chronological series. The method steps of FIG. 10 can represent one iteration of a cycle, the cycle being repeated for each frame received 100 in sequence.

Based on the received 100 frame, a patient support surface can be identified 101. The identification 101 of the patient support surface can be automated by a computing system. The patient support surface can correspond to the bed 40 of FIG. 3, or any other object or area on or about which a patient can be monitored. A nominal location of the patient support surface can be identified 101 based on multiple frames. Identification 101 of the patient support surface can include determining the three dimensional coordinates (e.g., along the X, Y, and Z axes) of one or more surfaces of the bed 40. Identification 101 of the patient support surface can include determining the three dimensional coordinates of one or more planes forming the bed 40. Identification 101 of the patient support surface can include identifying one or more boundaries of the patient support surface. Identification 101 of the patient support surface can be performed with the use of a template, as discussed herein.

The method can further include setting 102 at least one threshold based on the identified 101 patient support surface. Setting 102 the at least one threshold can comprise setting one or more height thresholds, setting one or more lower thresholds, and/or setting one or more vertical thresholds. Techniques for setting each of the height thresholds, the lower thresholds, and the vertical thresholds are discussed herein. Each height threshold can be set 102 along a two dimensional plane directly above, and parallel to, the location of the identified 101 patient support surface. Each lower threshold can be set 102 to correspond to at least one area below and laterally offset from the location of the identified 101 patient support surface. Two lower thresholds can be set 102 on the left side and the right side of the patient support surface. Each vertical threshold can be set 102 along a respective vertical plane extending upward from a respective one of the plurality of edges of the patient support surface. Two vertical thresholds can be set 102 on the left and the right side of the patient support surface.

The method can further include identifying 103 one or more patient locations based on the three dimensional information. Identifying 103 the one or more patient locations can include separating pixel information indicative of a patient location from pixel information that is irrelevant to a patient location. In some cases, pixels directly above any of the identified 101 patient support surface or the at least one lower threshold (if a lower threshold is set 102) can be assumed to be part of the patient. Separating the pixel information can include separating the pixels directly above any of the identified 101 patient support surface or the at least one lower threshold from pixels in the frame that are not directly above either of the identified 101 patient support surface or the at least one lower threshold. Separating the pixels can focus a detection algorithm on the space where the patient is expected to be and can ignore the areas where a patient is not likely to be (or unlikely to fall from). Separating can include distinguishing between those pixels directly above any of the identified 101 patient support surface or the at least one lower threshold from all other pixels of the frame. Pixels directly above any of the identified 101 patient support surface or the at least one lower threshold can be binned for subsequent analysis. Information concerning pixels that are not directly above either of the identified 101 patient support surface or the at least one lower threshold can be deleted or disregarded in subsequent analysis. Separating can include only analyzing the three dimensional information for pixels that are directly above any of the identified 101 patient support surface or the at least one lower threshold to identify 103 a patient location.

In some embodiments, one or more patient locations can be identified 103 by normalizing the pixels likely associated with the patient, as discussed herein. Part or all of the patient can be identified 103 based on a plurality of pixels being grouped together, as discussed herein. Identifying 103 the one or more patient locations can include detecting one or more patient surface outlines based on a pixel grouping. Identifying 103 the one or more patient locations can include detecting pixels associated with the patient generally or detecting particular features of a patient, such as a head, chest, arm, leg, and/or other part, as discussed herein. The one or more patient locations can be identified 103 based on various detection criteria, as discussed herein.

The method can further include comparing 104 the one or more patient locations to the threshold. The comparing 104 step can determine whether any part of the patient, or a particular part of the patient (e.g., a head) traverse any one of the set 102 thresholds. In some cases, a representative metric for an identified 103 patient location (e.g., a geometric center, average pixel height, volume) can be compared 104 to the threshold. In some embodiments, a minimum volume of a grouping of pixels may be needed to trip the threshold, wherein a grouping of pixel associated with a volume less than the minimum may not trip the threshold.

If one or more of the patient locations traverse 105 the threshold, an indication can be generated 106. Generating 106 the indication can include changing a fall risk status of a patient (e.g., raising the fall risk from low to high), storing a record of the event in memory, and/or issuing an alert (e.g., sounding an alarm perceivable by a healthcare professional and/or an indication on a screen). Different output can be generated 106 based on which type of threshold (height thresholds, lower thresholds, or vertical thresholds) was traversed. The different threshold types may escalate a fall risk state differently or trigger the generation 106 of different indications. For example, the tripping of a height threshold may generate a minor warning associated with low urgency, the tripping of a vertical threshold may generate a moderate warning associated with moderate urgency, and the tripping of a lower threshold may generate a severe warning associated with high urgency. Different alarms can be generated 106 based on which of these types of thresholds was tripped, with the types of alarms most likely to be noticed by a healthcare professional being generated 106 if one of lower thresholds is tripped while a less obtrusive alarm is generated if the height threshold is tripped.

The cycle of the method can then be repeated with the reception 100 of the next frame of the chronological series. If the one or more patient locations do not traverse 105 the threshold in the next iteration, then the fall risk can be lowered and/or an alert can be canceled. It is noted that the steps of the method of FIG. 10 can be performed in various orders, as discussed herein in connection with FIG. 5.

Figure 11:
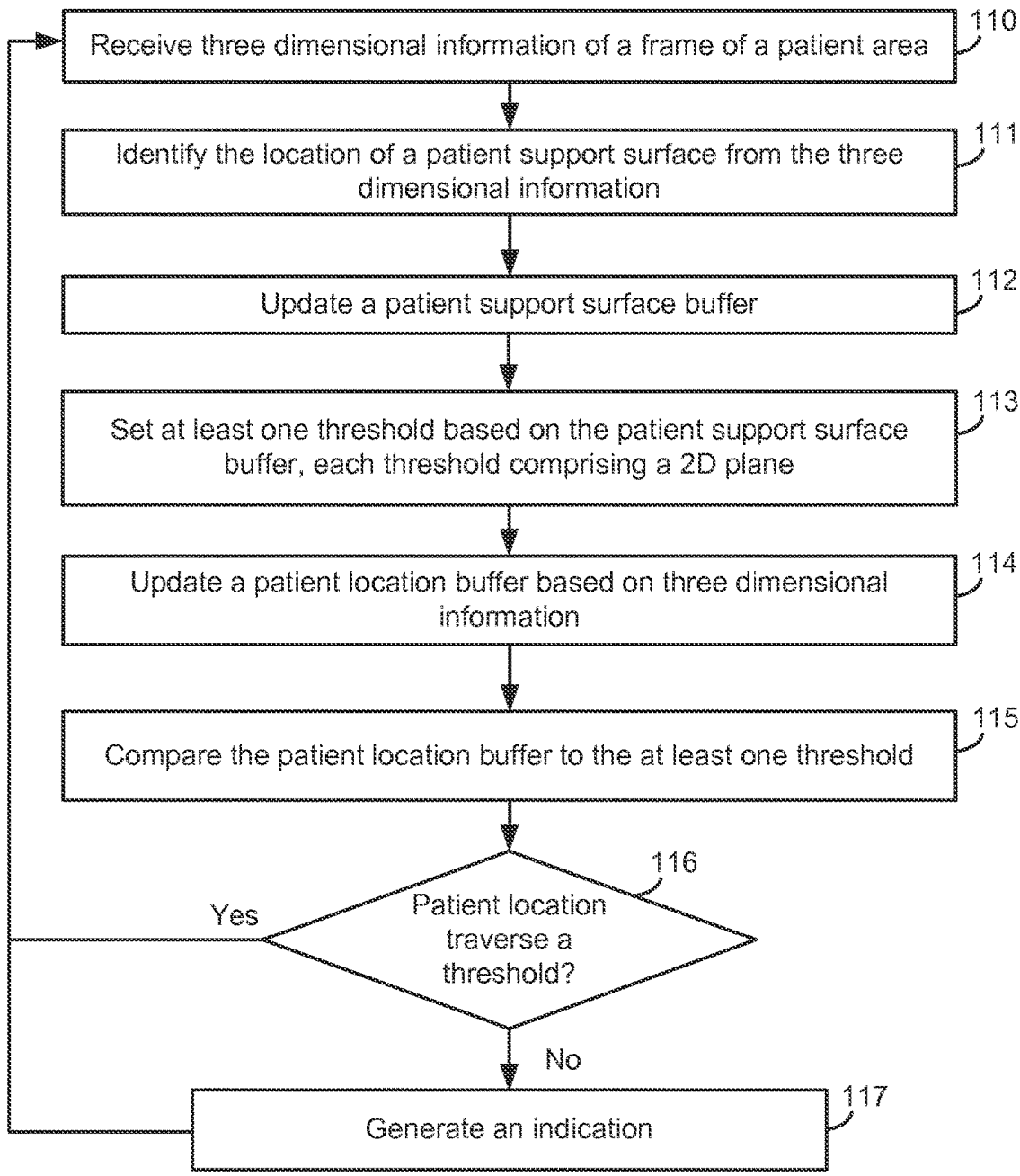
FIG. 11 is another flow chart of a method for monitoring a patient in three dimensions.

Various embodiments of the present disclosure can employ one or more buffers when monitoring a patient. The method of FIG. 11 outlines ways in which one or more buffers can be used in patient monitoring. It is noted that the method of FIG. 11 is similar to the methods of FIGS. 5-6 with the difference that FIG. 11 is directed to using buffers to establish various type of thresholds (e.g., height thresholds, lower thresholds, and vertical thresholds) while the methods of FIG. 5-6 focus on establishing height thresholds. Any of the techniques referenced in connection with the methods of FIGS. 5-6 and 10 can be applied to the method of FIG. 11. The method could be performed by a computing system as described herein. The method of FIG. 11 can refer to the same embodiment of the method of FIG. 10, wherein the flowcharts highlight different aspects of the method. Alternatively, the method of FIG. 11 can be implemented separately from the method of FIG. 10.

The method of FIG. 11 includes receiving 110 three dimensional information of a frame of a patient area. The reception 110 step can be performed in various ways described herein. The received 110 three dimensional information can include receiving a whole frame, receiving pixel information (e.g., pixel coordinates), and/or any information that can be used in patient monitoring. The method can further including identifying 111 the location of a patient support surface from the three dimensional information. The location of the patient support surface can be identified 111 using any technique referenced herein, including by use of a template.

A patient support surface buffer can be updated 112 based on the identified 111 location of the patient support surface. The buffer can contain coordinate information for each pixel that defines or is otherwise associated with the patient support surface. Information concerning the location of the patient support surface can be stored in the patient support surface buffer. In particular, information concerning the location of the patient support surface from different received 110 frames (e.g., the sequential frames of a chronological series of frames) can be stored together in the buffer. The building up of frames over time can facilitate the calculation of a nominal location of the patient support surface. Updating 112 the patient support surface buffer can include calculating the nominal location of the patient support surface based on the frame information collected in the patient support surface buffer, as described herein. Updating 112 a patient support surface buffer can include adding the identified 111 location of the patient support surface from the most recently received 110 frame to the patient support surface buffer, as discussed herein.

The method can further include setting 113 at least one threshold based on the patient support surface buffer. As discussed above, a location of patient support surface can be calculated from all of the identified 111 locations of the patient support surfaces from the patient support surface buffer (e.g., over 32 frames) as a nominal location of the patient support surface. The at least one threshold can be set 113 based on the aggregated location from all of the identified 111 locations of the patient support surface buffer. For example, the one or more thresholds can be set 113 based on the nominal location of the patient support surface. Various options for setting a threshold are discussed herein. Setting 113 the at least one threshold can comprise setting one or more height thresholds, setting one or more lower thresholds, and/or setting one or more vertical thresholds based on the nominal location of the patient support surface. Each height threshold can be set 113 along a two dimensional plane directly above, and parallel to, the nominal location of the patient support surface. Each lower threshold can be set 113 to correspond to at least one area below and laterally offset from the nominal location of the patient support surface. Two lower thresholds can be set 113 on the left and the right side of the patient support surface. Each vertical threshold can be set 113 along a respective vertical plane extending upward from a respective one of the plurality edges of the nominal location of the patient support surface. Two vertical thresholds can be set 113 on the left and the right side of the nominal location of the patient support surface.

The method can further include updating 114 a patient location buffer based on three dimensional information concerning the three dimensional space within the frame. The patient location buffer can contain information concerning the location of one or more features of a patient on the patient support surface from a plurality of frames. The patient location information in the patient location buffer can be from the same frames as the location information within the patient support surface buffer. Alternatively, the patient location information in the patient location buffer can be limited to three dimensional information concerning a reduced volume of the three dimensional space, such as the three dimension space directly above the patient support surface and/or directly above the at least one lower threshold (if set 113), and may not include three dimensional information concerning areas other than the space directly above the patient support surface and/or directly above the at least one lower threshold.

In some embodiments, identification of a location of one or more features of a patient can be performed based on the three dimensional information concerning space directly above the patient support surface and/or directly above the at least one lower threshold based on the most recently received 110 frame, and the one or more locations can be added to the patient location buffer in the update 114, wherein the patient location buffer contains the locations of the patient (e.g., locations of particular parts of the patient) identified for each of a plurality of frames. The locations can be averaged or in some manner aggregated to determine the aggregate location of part or all of the patient. Alternatively, the update 114 can include adding the three dimensional information concerning the space directly above the patient support surface and/or directly above the at least one lower threshold based on the patient location buffer, wherein the patient location buffer can contain all of the three dimensional information concerning the space directly above the patient support surface and/or directly above the at least one lower threshold for each of a plurality of previously received 110 frames. In this manner, the buffer can contain raw data concerning the space directly above the patient support surface to the exclusion of data concerning space not directly above the patient support surface. The location of the patient can then be determined based on the data within the patient location buffer. A nominal patient location can be calculated from the three dimensional information concerning the space directly above the patient support surface and/or directly above the at least one lower threshold using a similar technique as calculating and/or updated a nominal location of the patient support surface. In some cases, only the three dimensional information above a patient support surface can be used as described above while the three dimensional information below the patient support surface is not used.

The method can further include comparing 115 the location of the patient to the one or more thresholds. The comparison can be performed according to any technique referenced herein. The comparing 115 step can determine whether any part of the patient, or a particular part of the patient traverse a set 113 threshold. If one or more of the patient locations traverse 116 the threshold, an indication can be generated 117. Generating 117 the indication can include changing a fall risk status of a patient (e.g., raising the fall risk from low to high), and/or issuing an alert (e.g., sounding an alarm or providing a notification on a screen). Generating 117 the indication can be performed in any manner referenced herein, including in any manner discussed in connection with FIG. 10. The cycle can then be repeated with the reception 110 of the next frame of the chronological series.

The flowchart and block diagrams in the FIGS. of the present disclosure illustrate the architecture, functionality, and operation of some possible implementations of systems, methods, and computer program products according to various embodiments of the present disclosure. In this regard, each step in the flowchart or arrangement of blocks may represent a component, module, segment, or portion of code, which comprises one or more executable instructions for implementing the specified logical function(s). It should also be noted that, in some alternative implementations, the functions noted in the steps may occur out of the order noted in the FIGS. or as otherwise described. For example, two steps shown in succession may, in fact, be executed substantially concurrently, or the steps may sometimes be executed in the reverse order, depending upon the functionality involved.

It is noted that reception of a frame (e.g., by a computing system from a camera) does not necessarily mean reception of all of the data of the frame sufficient to reconstruct the entire frame. Rather, reception of the frame can include reception of representative data (e.g., three dimensional coordinate information) that allows for calculation of a position or other values for performing the functions described herein.

The techniques described in this disclosure, including those of FIGS. 1-7 and those attributed to a monitoring system, a computing system, a processor, and/or control circuitry, and/or various constituent components, may be implemented wholly or at least in part, in hardware, software, firmware or any combination thereof. A processor, as used herein, refers to any number and/or combination of a microprocessor, a digital signal processor (DSP), an application specific integrated circuit (ASIC), a field-programmable gate array (FPGA), microcontroller, discrete logic circuitry, processing chip, gate arrays, and/or any other equivalent integrated or discrete logic circuitry. A "control circuitry" as used herein refers to at least one of the foregoing logic circuitry as a processor, alone or in combination with other circuitry, such as memory or other physical medium for storing instructions, as needed to carry about specified functions (e.g., processor and memory having stored program instructions executable by the processor for identifying a location of a patient support surface, setting a height threshold, a lower threshold, and/or a vertical threshold based on the location of the patient support surface, identifying one or more patient locations directly above the patient support surface, and comparing the one or more patient locations to the one or more thresholds). The functions referenced herein and those functions of FIGS. 1-11, may be embodied as firmware, hardware, software or any combination thereof as part of a computing system specifically configured (e.g., with programming) to carry out those functions, such as in means for performing the functions referenced herein. The steps described herein may be performed by a single processing component or multiple processing components, the latter of which may be distributed amongst different coordinating devices. In this way, the computing system may be distributed between multiple devices, including part of a camera and part of a computer. In addition, any of the described units, modules, or components may be implemented together or separately as discrete but interoperable logic devices of a computing system. Depiction of different features as modules or units is intended to highlight different functional aspects and does not necessarily imply that such modules or units must be realized by separate hardware or software components and/or by a single device. Rather, functionality associated with one or more modules or units, as part of a computing system, may be performed by separate hardware or software components, or integrated within common or separate hardware or software components of the computing system.

When implemented in software, the functionality ascribed to a computing system may be embodied as instructions on a physically embodied computer-readable medium such as RAM, ROM, NVRAM, EEPROM, FLASH memory, magnetic data storage media, optical data storage media, or the like, the medium being physically embodied in that it is not a carrier wave, as part of the computing system. The instructions may be executed to support one or more aspects of the functionality described in this disclosure.

The particular embodiments described below are not intended to limit the scope of the present disclosure as it may be practiced in a variety of variations and environments without departing from the scope and intent of the invention. Thus, the present disclosure is not intended to be limited to the embodiments shown, but is to be accorded the widest scope consistent with the principles and features described herein. Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What is claimed is:

1. A patient monitoring system for monitoring a patient area, the system comprising:
    a sensor configured to output a plurality of frames, the plurality of frames containing three dimensional information of the patient area, wherein the three dimensional information comprises grid positions of a plurality of pixels represented by coordinates along X- and Y-axes and depth of each pixel relative to a floor along a Z-axis; and
    control circuitry configured to:
    receive the three dimensional information of the plurality of frames;
    identify a location of a patient support surface by segmenting the three dimensional information into candidate areas and grouping one or more planar surfaces in the candidate areas based on pixel depth;
    set at least one threshold above the location of the patient support surface on the Z-axis;
    identify one or more patient locations based on pixels that are above a depth of the patient support surface and within the location of the patient support surface;
    compare the one or more patient locations to the at least one threshold; and
    generate an output for display on a user interface based on the one or more patient locations traversing the at least one threshold.

2. The patient monitoring system of claim 1, wherein the control circuitry is configured to determine one or more boundaries corresponding to the location of the patient support surface based on a contrast in height from a given surface to the floor using the three dimensional information.

3. The patient monitoring system of claim 1, wherein the control circuitry is configured to repeat the identifying the location of the patient support surface and the setting of the at least one threshold steps to dynamically adjust the at least one threshold to account for changes in the location of the patient support surface.

4. The patient monitoring system of claim 1, wherein the control circuitry configured to group non-coplanar ones of the one or more planar surfaces.

5. The patient monitoring system of claim 1, wherein the control circuitry is configured to interpolate the one or more planar surfaces.

6. The patient monitoring system of claim 1, wherein the control circuitry is configured to set the at least one threshold to extend laterally along the X- and Y-axes within the location of the patient support surface.

7. The patient monitoring system of claim 1, wherein the control circuitry is configured to set the at least one threshold to extend laterally along X- and Y-axes beyond the location of the patient support surface.

8. The patient monitoring system of claim 1, wherein the control circuitry is configured to detect pixels associated with bodily features of a patient.

9. The patient monitoring system of claim 8, wherein the control circuitry is configured to identify the one or more patient locations based on the pixels associated with the bodily features of the patient.

10. The patient monitoring system of claim 1, wherein the control circuitry is configured to identify the one or more patient locations based on a grouping of pixels with a quantity above a threshold amount that are above the depth of the patient support surface and within the location of the patient support surface.

11. A method for processing a chronological series of frames containing three dimensional information comprising grid positions of a plurality of pixels represented by coordinates along X- and Y-axes and depth of each pixel relative to a floor along a Z-axis, the plurality of pixels generated by a camera to monitor a patient in a patient area by performing the following steps, each step performed at least in part by a computing system:
    receiving the three dimensional information of a plurality of frames;
    identifying a location of a patient support surface by segmenting the three dimensional information into candidate areas and grouping one or more planar surfaces in the candidate areas based on pixel depth;
    setting at least one threshold above the location of the patient support surface on the Z-axis;
    identifying one or more patient locations based on pixels that are above a depth of the patient support surface and within the location of the patient support surface;
    comparing the one or more patient locations to the at least one threshold; and
    generating an output for display on a user interface based on the one or more patient locations traversing the at least one threshold.

12. The method of claim 11, further comprising determining one or more boundaries corresponding to the location of the patient support surface based on a contrast in height from a given surface to the floor using the three dimensional information.

13. The method of claim 11, further comprising repeating the identifying the location of the patient support surface and the setting of the at least one threshold steps to dynamically adjust the at least one threshold to account for changes in the location of the patient support surface.

14. The method of claim 11, further comprising grouping non-coplanar ones of the one or more planar surfaces.

15. The method of claim 11, further comprising interpolating the one or more planar surfaces.

16. The method of claim 11, further comprising setting the at least one threshold to extend laterally along the X- and Y-axes within the location of the patient support surface.

17. The method of claim 11, further comprising setting the at least one threshold to extend laterally along X- and Y-axes beyond the location of the patient support surface.

18. The method of claim 11, further comprising:
 detecting pixels associated with bodily features of a patient; and
 identifying the one or more patient locations based on the pixels associated with the bodily features of the patient.

19. The method of claim 11, further comprising identifying the one or more patient locations based on a grouping of pixels with a quantity above a threshold amount that are above the depth of the patient support surface and within the location of the patient support surface.

20. Non-transitory computer-readable media comprising program code that when executed by a programmable processor causes execution of a method for processing a chronological series of frames containing three dimensional information comprising grid positions of a plurality of pixels represented by coordinates along X- and Y-axes and depth of each pixel relative to a floor along a Z-axis, the plurality of pixels generated by a camera to monitor a patient in a patient area, the non-transitory computer-readable media comprising:
 computer program code for receiving the three dimensional information of a plurality of frames;
 computer program code for identifying a location of a patient support surface by segmenting the three dimensional information into candidate areas and grouping one or more planar surfaces in the candidate areas based on pixel depth;
 computer program code for setting at least one threshold above the location of the patient support surface on the Z-axis;
 computer program code for identifying one or more patient locations based on pixels that are above a depth of the patient support surface and within the location of the patient support surface;
 computer program code for comparing the one or more patient locations to the at least one threshold; and
 computer program code for generating an output for display on a user interface based on the one or more patient locations traversing the at least one threshold.

* * * * *